US012428458B2

(12) United States Patent
Tamai et al.

(10) Patent No.: US 12,428,458 B2
(45) Date of Patent: Sep. 30, 2025

(54) THERAPEUTIC AGENT FOR PSORIASIS

(71) Applicants: StemRIM Inc., Osaka (JP); OSAKA UNIVERSITY, Osaka (JP)

(72) Inventors: Katsuto Tamai, Osaka (JP); Takashi Shimbo, Osaka (JP); Takehiko Yamazaki, Osaka (JP)

(73) Assignees: STEMRIM INC., Osaka (JP); OSAKA UNIVERSITY, Osaka (JP)

( * ) Notice: Subject to any disclaimer, the term of this patent is extended or adjusted under 35 U.S.C. 154(b) by 0 days.

(21) Appl. No.: 17/817,084

(22) Filed: Aug. 3, 2022

(65) Prior Publication Data

US 2022/0380420 A1 Dec. 1, 2022

Related U.S. Application Data

(63) Continuation of application No. 16/967,919, filed as application No. PCT/JP2019/004330 on Feb. 7, 2019, now abandoned.

(30) Foreign Application Priority Data

Feb. 8, 2018 (JP) ................................ 2018-020687

(51) Int. Cl.
| C07K 14/47 | (2006.01) |
| A61K 38/00 | (2006.01) |
| A61P 17/06 | (2006.01) |

(52) U.S. Cl.
CPC .............. *C07K 14/47* (2013.01); *A61P 17/06* (2018.01); *A61K 38/00* (2013.01)

(58) Field of Classification Search
None
See application file for complete search history.

(56) References Cited

U.S. PATENT DOCUMENTS

| 3,896,810 | A | 7/1975 | Akiyama |
| 4,732,155 | A | 3/1988 | Zetter et al. |
| 5,133,755 | A | 7/1992 | Brekke |
| 5,661,127 | A | 8/1997 | Bhatnagar et al. |
| 5,760,261 | A | 6/1998 | Guttag |
| 5,851,986 | A | 12/1998 | Takada et al. |
| 5,902,799 | A | 5/1999 | Herrmann et al. |
| 6,723,319 | B1 | 4/2004 | Ito et al. |
| 6,905,874 | B2 | 6/2005 | Berenson et al. |
| 7,220,723 | B2 | 5/2007 | Tracey et al. |
| 7,288,250 | B2 | 10/2007 | Newman et al. |
| 7,446,100 | B2 | 11/2008 | Pilarski |
| 7,470,538 | B2 | 12/2008 | Laughlin et al. |
| 7,585,504 | B2 | 9/2009 | Wu et al. |
| 7,632,802 | B2 | 12/2009 | Tessier et al. |
| 7,749,959 | B2 | 7/2010 | Tracey et al. |
| 7,829,097 | B2 | 11/2010 | Tsung et al. |
| 7,833,975 | B2 | 11/2010 | Okazawa |
| 7,939,057 | B2 | 5/2011 | Battista et al. |
| 8,114,668 | B2 | 2/2012 | Stolen et al. |
| 8,119,121 | B2 | 2/2012 | Fraser et al. |
| 8,551,470 | B2 | 10/2013 | Son et al. |
| 8,673,580 | B2 | 3/2014 | Tamai et al. |
| 9,623,078 | B2 | 4/2017 | Tamai et al. |
| 9,688,733 | B2 | 6/2017 | Tamai et al. |
| 9,919,010 | B2 | 3/2018 | Tamai et al. |
| 10,393,762 | B2 | 8/2019 | Fuhrmann et al. |
| 10,595,530 | B2 | 3/2020 | Goodman et al. |
| 10,626,153 | B2 | 4/2020 | Bianchi et al. |
| 2003/0003482 | A1 | 1/2003 | Halle et al. |
| 2003/0060410 | A1 | 3/2003 | Tracey et al. |
| 2004/0028681 | A1 | 2/2004 | Ito et al. |
| 2004/0031072 | A1 | 2/2004 | La Rosa et al. |
| 2004/0156851 | A1 | 8/2004 | Newman |
| 2004/0191246 | A1 | 9/2004 | Connelly et al. |
| 2004/0242481 | A1 | 12/2004 | Bianchi et al. |
| 2004/0249448 | A1 | 12/2004 | Gault |
| 2004/0265971 | A1 | 12/2004 | Sato et al. |
| 2005/0014255 | A1 | 1/2005 | Tang et al. |
| 2005/0101564 | A1 | 5/2005 | Pilarski |
| 2006/0003312 | A1 | 1/2006 | Blau et al. |
| 2006/0035851 | A1 | 2/2006 | Bianchi et al. |
| 2006/0039896 | A1 | 2/2006 | Kleinsek et al. |
| 2006/0069064 | A1 | 3/2006 | Khaldoyanidi |
| 2006/0111287 | A1 | 5/2006 | Bianchi |
| 2006/0183667 | A1 | 8/2006 | Jonassen et al. |

(Continued)

FOREIGN PATENT DOCUMENTS

| AU | 2003228099 A1 | 1/2004 |
| AU | 2004203732 A1 | 7/2004 |

(Continued)

OTHER PUBLICATIONS

Nickoloff et al. (J Clin Invest. 2004;113(12):1664-1675) (Year: 2004).*

Tamilselvi et al. (Scand J Immunol. Dec. 2013;78(6):545-53) (Year: 2013).*

Fujii, Makiko et al., "Roles of Bone Morphogenetic Protein Type I Receptors and Smad Proteins in Osteoblast and Chondroblast Differentiation." Molecular Biology of the Cell, 10(11): 3801-3813, (Year: 1999).

Fukushima, Norihide et al., "Registry Report on Heart Transplantation in Japan (Jun. 2016)." Circulation Journal, 81: 298-303, (Year: 2017).

Funayama, Akira et al. "Cardiac nuclear high mobility group box 1 prevents the development of cardiac hypertrophy and heart failure." Cardiovascular Research 99(4): 657-664, (Year: 2013).

(Continued)

*Primary Examiner* — Sergio Coffa

(74) *Attorney, Agent, or Firm* — SALIWANCHIK, LLOYD & EISENSCHENK

(57) ABSTRACT

The present inventors discovered that an HMGB1 fragment peptide having a specific amino acid sequence exhibits an effect of suppressing erythema, scaling (desquamation), and thickening (infiltration) of the skin in an animal model of psoriasis. Based on these findings, pharmaceutical compositions for the prevention and/or treatment of psoriasis, which comprise the HMGB1 fragment peptide having the specific amino acid sequence are provided.

7 Claims, 8 Drawing Sheets

Specification includes a Sequence Listing.

(56) References Cited

U.S. PATENT DOCUMENTS

| | | |
|---|---|---|
| 2007/0154529 A1 | 7/2007 | Bullerdiek |
| 2007/0238663 A1 | 10/2007 | Capogrossi et al. |
| 2008/0038309 A1 | 2/2008 | Fumero et al. |
| 2008/0064065 A1 | 3/2008 | Kim et al. |
| 2009/0053277 A1 | 2/2009 | Nagaya et al. |
| 2009/0062187 A1 | 3/2009 | Bianchi et al. |
| 2009/0202500 A1 | 8/2009 | Tamai et al. |
| 2010/0040608 A1* | 2/2010 | Wahren-Herlenius ............... A61P 17/00 424/139.1 |
| 2010/0280493 A1 | 11/2010 | Nayak |
| 2011/0097309 A1 | 4/2011 | Tamai et al. |
| 2012/0237504 A1 | 9/2012 | Brooks et al. |
| 2012/0251510 A1 | 10/2012 | Tamai et al. |
| 2014/0206619 A1 | 7/2014 | Tamai et al. |
| 2015/0273017 A1* | 10/2015 | Tamai ............... C07K 14/4718 514/16.4 |
| 2016/0032248 A1 | 2/2016 | Short et al. |
| 2018/0055886 A1 | 3/2018 | Tamai et al. |
| 2018/0072785 A1 | 3/2018 | Tamai et al. |
| 2019/0343924 A1 | 11/2019 | Tamai et al. |
| 2020/0038486 A1 | 2/2020 | Tamai et al. |
| 2020/0291359 A1 | 9/2020 | Tamai et al. |
| 2020/0369736 A1 | 11/2020 | Tamai et al. |
| 2021/0024594 A1 | 1/2021 | Tamai et al. |
| 2021/0163552 A1 | 6/2021 | Nihashi et al. |
| 2021/0347839 A1 | 11/2021 | Tamai et al. |
| 2022/0009976 A1 | 1/2022 | Tamai et al. |
| 2022/0265787 A1 | 8/2022 | Tamai et al. |

FOREIGN PATENT DOCUMENTS

| | | |
|---|---|---|
| AU | 2007315073 A1 | 5/2008 |
| AU | 2012248676 A1 | 11/2013 |
| CA | 2325226 A1 | 5/2001 |
| CA | 2512512 A1 | 7/2004 |
| CA | 2636788 A1 | 5/2008 |
| CN | 1193092 C | 3/2005 |
| CN | 1671742 A | 9/2005 |
| CN | 1878793 A | 12/2006 |
| CN | 101132811 A | 2/2008 |
| CN | 101291955 A | 10/2008 |
| CN | 100447154 C | 12/2008 |
| CN | 101366728 A | 2/2009 |
| CN | 101374538 A | 2/2009 |
| CN | 101528266 A | 9/2009 |
| CN | 101641372 A | 2/2010 |
| CN | 102076350 A | 5/2011 |
| CN | 102247392 A | 11/2011 |
| CN | 102443064 A | 5/2012 |
| CN | 103687946 A | 3/2014 |
| CN | 102711777 B | 4/2015 |
| CN | 104884076 A | 9/2015 |
| CN | 104955470 A | 9/2015 |
| CN | 105026553 A | 11/2015 |
| CN | 107188948 A | 9/2017 |
| CN | 110494154 A | 11/2019 |
| EP | 1114862 A2 | 7/2001 |
| EP | 1459759 A1 | 9/2004 |
| EP | 0791601 B1 | 4/2005 |
| EP | 2039367 A1 | 3/2009 |
| EP | 2055308 A1 | 6/2009 |
| EP | 2284255 A1 | 2/2011 |
| EP | 2301559 A1 | 3/2011 |
| EP | 2301560 A1 | 3/2011 |
| EP | 2601971 A1 | 6/2013 |
| EP | 2703487 A1 | 3/2014 |
| EP | 2913059 A1 | 9/2015 |
| EP | 2913058 B1 | 12/2017 |
| EP | 2494977 B1 | 6/2018 |
| EP | 3556378 A1 | 10/2019 |
| EP | 3358011 B1 | 3/2020 |
| EP | 3719117 A1 | 10/2020 |
| EP | 3750553 A1 | 12/2020 |
| JP | 3018313 B2 | 3/2000 |
| JP | 2003505506 A | 2/2003 |
| JP | 3421741 B2 | 6/2003 |
| JP | 2005508913 A | 4/2005 |
| JP | 2005512507 A | 5/2005 |
| JP | 2005537253 A | 12/2005 |
| JP | 2006010619 A | 3/2006 |
| JP | 2006517537 A | 7/2006 |
| JP | 2006523085 A | 10/2006 |
| JP | 2008507505 A | 3/2008 |
| JP | 2008511300 A | 4/2008 |
| JP | 2010503630 A | 2/2010 |
| JP | 4982739 B2 | 7/2012 |
| JP | 5134772 B2 | 1/2013 |
| JP | 5814549 B2 | 11/2015 |
| JP | 7405345 B2 | 12/2023 |
| KR | 10 2005 0054907 A | 6/2005 |
| KR | 20090078304 A | 7/2009 |
| KR | 101448800 B1 | 10/2014 |
| KR | 10 2015 0103660 A | 9/2015 |
| KR | 101636139 B1 | 7/2016 |
| RU | 2005102593 A | 10/2005 |
| RU | 2410125 C2 | 1/2011 |
| RU | 2010148785 A | 6/2012 |
| RU | 2599448 C2 | 10/2016 |
| WO | 0108683 A1 | 2/2001 |
| WO | 0234292 A1 | 5/2002 |
| WO | 02074337 A1 | 9/2002 |
| WO | 02088181 A2 | 11/2002 |
| WO | 02092004 A2 | 11/2002 |
| WO | 03026691 A2 | 4/2003 |
| WO | 03043651 A1 | 5/2003 |
| WO | 2004004763 A2 | 1/2004 |
| WO | 2004004770 A1 | 1/2004 |
| WO | 2004044001 A1 | 5/2004 |
| WO | 2004046345 A2 | 6/2004 |
| WO | 2004061456 A2 | 7/2004 |
| WO | 2005025604 A2 | 3/2005 |
| WO | 2005074984 A1 | 8/2005 |
| WO | 2005087797 A1 | 9/2005 |
| WO | 2006008779 A1 | 1/2006 |
| WO | 2006010628 A1 | 2/2006 |
| WO | 2006024547 A2 | 3/2006 |
| WO | 2006047820 A1 | 5/2006 |
| WO | 2006077614 A1 | 7/2006 |
| WO | 2006080434 A1 | 8/2006 |
| WO | 2006100651 A1 | 9/2006 |
| WO | 2006114805 A2 | 11/2006 |
| WO | 2007015546 A1 | 2/2007 |
| WO | 2007031100 A1 | 3/2007 |
| WO | 2007061762 A2 | 5/2007 |
| WO | 2007076200 A2 | 7/2007 |
| WO | 2007130725 A2 | 11/2007 |
| WO | 2008018641 A1 | 2/2008 |
| WO | 2008031612 A1 | 3/2008 |
| WO | 2008053892 A1 | 5/2008 |
| WO | 2008104090 A1 | 9/2008 |
| WO | 2008155659 A2 | 12/2008 |
| WO | 2009133939 A1 | 11/2009 |
| WO | 2009133940 A1 | 11/2009 |
| WO | 2009133943 A1 | 11/2009 |
| WO | 2011046570 A1 | 4/2011 |
| WO | 2011052668 A1 | 5/2011 |
| WO | 2012147470 A1 | 11/2012 |
| WO | 2014065347 A1 | 5/2014 |
| WO | 2014065348 A1 | 5/2014 |
| WO | 2014191364 A1 | 12/2014 |
| WO | 2016184795 A1 | 11/2016 |
| WO | 2016185476 A1 | 11/2016 |
| WO | 2018139562 A1 | 8/2018 |
| WO | 2018186480 A1 | 10/2018 |
| WO | 2018199107 A1 | 11/2018 |
| WO | 2019107530 A1 | 6/2019 |
| WO | 2019107566 A1 | 6/2019 |
| WO | 2019156137 A1 | 8/2019 |
| WO | 2020071519 A1 | 10/2019 |
| WO | 2020071520 A1 | 4/2020 |

(56) References Cited

FOREIGN PATENT DOCUMENTS

| WO | 2020158924 A1 | 8/2020 |
|---|---|---|
| WO | 2021201260 A1 | 10/2021 |

OTHER PUBLICATIONS

Gallina, Clara et al., "A New Paradigm in Cardiac Regeneration: The Mesenchymal Stem Cell Secretome." Stem Cells International, vol. 2015, Article ID 765846, pp. 1-10, (Year: 2015).
Germani, Antonia et al., "Pivotal Advance: High-mobility group box 1 protein-a cytokine with a role in cardiac repair." Journal of Leukocyte Biology, 81(1): 41-45, (Year: 2007).
Gong, Wei et al. "The Anti-Inflammatory Activity of HMGB1 A Box is Enhanced When Fused with C-Terminal Acidic Tail," Journal of Biomedicine and Biotechnology, vol. 2010, Article ID 915234, pp. 1-6 (Year: 2010).
Goto, et al., "Investigation of the application of myocardial regeneration inducing therapy using HMGB1 to cardiac infarction." Regenerative Medicine, 16: 289, Feb. 1, 2017.
Granero-Molto, F. et al., "Role of mesenchymal stem cells in regenerative medicine: application to bone and cartilage repair," Expert Opinion on Biological Therapy, 8(3): 255-268, (Year: 2008).
Gudjonsson, Johann E. & Elder, James T. "Chapter 18—Psoriasis." Fitzpatrick's Dermatology in General Medicine, 8th edition, New York: Mc-Graw Hill Medical, 2012, pp. 197-217.
Gueukdjian S. A. "Intra-Arterial Injections in the Treatment of Peripheral Vascular Disease." Postgrad Medical Journal, 31(351): 30-31, (Year: 1955).
Guillot, Loïc et al. "Response of Human Pulmonary Epithelial Cells to Lipopolysaccharide Involves Toll-like Receptor 4 (TLR4)-dependent Signaling Pathways." Journal of Biological Chemistry, 279(4): 2712-2718, Nov. 4, 2003.
Guo, Haiwei H. et al. "Protein tolerance to random amino acid change." Proceedings of the National Academy of Sciences 101(25):9205-9210, Jun. 22, 2004.
Guo, Jing et al. "Monocyte Chemotactic Protein-1 Promotes the Myocardial Homing of Mesenchymal Stem Cells in Dilated Cardiomyopathy." International Journal of Molecular Sciences, 14: 8164-8178, (Year: 2013).
Harris, Helena Erlandsson & Raucci, Angela "Alarmin(g) news about danger," EMBO Reports, 7(8): 774-778, Jul. 21, 2006.
Harrison, Craig A. et al., "Oxidation Regulates the Inflammatory Properties of the Murine S100 Protein S100A8." J. Biol. Chem., 274(13): 8561-8569, (Year: 1999).
Healthwise Staff, "Age-related Macular Degeneration," University of Michigan Health System, Aug. 2015, https:www.uofmhealth.org/health-library/hw176039.
He, Y.T., et al., "HMGB1 Ameliorates Inflammatory Bowel Disease by Inducing Circulating Mesenchymal Stem Cells." The 17th Congress of the Japanese Society for Regenerative Medicine, 2018, 34, Abstract.
Heil, Matthias et al., "An engineered heparin-binding form of VEGF-E (hbVEGF-E)," Angiogenesis, 6(3): 201-211, (Year: 2003).
Herrera, M.B. et al., "Exogenous mesenchymal stem cells localize to the kidney by means of CD44 following acute tubular injury," Kidney International, 2: 430-441, (Year: 2007).
Hiratsuka S. et al. "Tumour-mediated upregulation of chemoattractants and recruitment of myeloid cells predetermines lung metastasis," Natural Cell Biology, 8(12): 1369-1375, Nov. 26, 2006.
HMGBiotech, "BoxA from HMGB1, human & mouse, LPS-free." HMGBiotech Srl, 2008, C.F. e P.IVA 04942740962, http://www.hmgbiotech.com/products.php?ID=91, ,accessed Jan. 27, 2017 from internet>.
HMGBiotech, "BoxA from HMGB1, human & mouse, LPS-free-Datasheet." HMGBiotech Srl, 2008, Via Moretto da Brescia 25, 20133—Milano, Italy, http://www.hmgbiotech.com/upload/documenti/0515122144_boxa.
HNRPK_Human, Accession No. P61978, entry version 183, UniProtKB/Swiss-Prot, Sep. 12, 2018.
Hori, Osamu et al. "The Receptor for Advanced Glycation End Products (RAGE) Is a Cellular Binding Site for Amphoterin," Journal of Biological Chemistry, 270(43): 25752-25761, (Year: 1995).
Hornef, Mathias W., et al. "Toll-like Receptor 4 Resides in the Golgi Apparatus and Colocalizes with Internalized Lipopolysaccharide in Intestinal Epithelial Cells." J. Exp. Med., 195(5): 559-570, (Year: 2002).
Hruby, V.J., "Designing Peptide Receptor Agonists and Antagonists." Nature Reviews Drug Discovery, 1: 847-858, Nov. 1, 2002.
Hu, Zhen et al. "Role of high-mobility group box 1 protein in inflammatory bowel disease." Inflammation Research 64(8): 557-563, (Year 2015).
Huttunen, Henri J. et al. "Receptor for Advanced Glycation End Products-binding COOH-terminal Motif of Amphoterin Inhibits Invasive Migration and Metastasis," Cancer Research, 62: 4805-4811, Aug. 15, 2002.
Ichinose, Kunihiro et al., "Antiangiogenic Endostatin Peptide Ameliorates Renal Alterations in the Early Stage of a Type 1 Diabetic Nephropathy Model." Diabetes, 54(10): 2891-2903, (Year: 2005).
Instruction Manual of HiTrap chelating HP (Amersham Biosciences), 2003, pp. 1-6.
Ishikane, Shin, "Therapeutic application of allogenic fetal membrane-derived mesenchymal stem cells transplantation in regenerative medicine." Pharmaceutical Bulletin of Fukuoka University, 11(0): 17-25, (Year: 2011).
Ishikane, Shin et al., "Development of multi-growth factor secreted fetal membrane-derived mesenchymal stem cell sheets." Grants-in-Aid for Scientific Research, pp. 1-6, (Year: 2014).
Jansen, Jan et al., "Transplantation of hematopoietic stem cells from the peripheral blood," Journal of Cellular and Molecular Medicine, 9(1): 37-50, (Year: 2005).
Jayaraman, Lata et al. "High mobility group protein-1 (HMG-1) is a unique activator of p53." Genes & Development, 12(4): 462-472, (Year: 1998).
Jiang, Yuehua et al. "Pluripotency of mesenchymal stem cells derived from adult marrow." Nature, 418(6893): 41-49, (Year: 2002).
Jiao, Chunhua et al., "Researchers find nerve damage may precede diabetic retinopathy," EurekAlert! Science News, Apr. 2016, https://www.eurekalert.org/pub_releases/2016-04/uoih-rfv042616.php.
Jin, Y. "Isolating culture and induced differentiation of marrow mesenchyma stem cells," Principles and Protocols of Tissue Engineering, Jun. 2004, 277-278 (English translation attached).
Justice, Monica J. & Dhillon, Paraminder "Using the mouse to model human disease: increasing validity and reproducibility." Dis Model Mech. 9(2):101-103, Feb. 1, 2016.
Kaneda et al., "Tissue repair mechanism by bone-marrow-derived stem cells." Experimental Mediciner, 2013, 31(5): 655-661.
Kaneko, Masahiro et al. "Abstract 11250: Bone Marrow Mononuclear Cell Transplantation Improves Cardiac Function in Ischemic Cardiomyopathy via High Mobility Group Box 1 Released from Dead Donor Cells." Circulation 126:A11250, Mar. 28, 2018.
Kassis, I. et al. "Isolation of mesenchymal stem cells from G-CSF mobilized human peripheral blood using fibrin microbeads," Bone Marrow Transplantation, 37(10): 967-976, (Year: 2006).
Kawabata, Hideyuki et al., "High Mobility Group Box 1 Is Upregulated After Spinal Cord Injury and Is Associated With Neuronal Cell Apoptosis," Spine, 35(11): 1109-1115, (Year: 2010).
Kern, Susanne et al. "Comparative Analysis of Mesenchymal Stem Cells from Bone Marrow, Umbilical Cord Blood, or Adipose Tissue," Stem Cells, 24(5): 1294-1301, (Year: 2006).
Kessler, Michael W. & Grande, Daniel A. "Tissue Engineering and Cartilage." Organogenesis, 4(1): 28-32, (Year: 2008).
Kido, Takashi et al., "Abstract 15756: The Administration of High-morbidity Group Box 1 Fragment Prevents Deterioration of Cardiac Performance by Enhancement of Bone-marrow Mesenchymal Stem Cells Homing in the Delta-sarcoglycan-deficient Hamster." Circulation, Nov. 2017, 136(Suppl 1): Abstract.
Kikuchi, K. et al., "HMGB1 as a therapeutic target in spinal cord injury: A hypothesis for novel therapy development (Review)," Experimental and Therapeutic Medicine, 2: 767-770, (Year: 2011).

(56) References Cited

OTHER PUBLICATIONS

Kikuchi, K. et al. "Systemic administration of HMGB1 improves bleomycin-induced skin fibrosis by locally accumulating bone marrow mesenchymal stem cells." Regenerative Medicine, Feb. 1, 2017, 16: 422.

Kim, Sang-Soo et al. "Skin Regeneration Using Keratinocytes and Dermal Fibroblasts Cultured on Biodegradable Microspherical Polymer Scaffolds," Journal of Biomedical Materials Research Part B: Applied Biomaterials, 75(2): 369-377, (Year: 2005).

Kirov, Sergei A. et al. "In Vivo 2-Photon Microscopy Reveals G-CSF Enhanced Mobilization and Targeting of Neo-Endogenous Bone Marrow Stromal Cells to Stroke Injury Sites." Stroke, Apr. 2009, 40(4): 1-2, e133, Abstract No. 107.

Kitahara, Tatsuro et al. "High-Mobility Group Box 1 Restores Cardiac Function After Myocardial Infarcation in Transgenic Mice," Cardiovascular Research, European Society of Cardiology, 80: 40-46, Oct. 1, 2008.

Tagami, Kozo et al. "Elevation of serum high-mobility group box 1 protein during granulocyte colony-stimulating factorinduced peripheral blood stem cell mobilisation." British Journal of Haematology, 135(4): 567-569, (Year: 2006).

Tagliafico, Enrico et al. "TGFB/BMP activate the smooth muscle/bone differentiation programs in mesoangioblasts." Journal of Cell Science, 117(19): 4377-4388, (Year: 2004).

Takahashi, Kunihiko et al. "Modulated Inflammation by Injection of High-Mobility Group Box 1 Recovers Post-Infarction Chronically Failing Heart." Circulation, 118(14 Suppl): S106-S114, (Year: 2008).

Takahashi, K. et al., "Effects of HMGB1 on PostInfarction Chronic Heart Failure—Novel Mechanism Regarding Therapeutic Effects of Cell Therapy." Supplement, 27 I-E-19:S189, (Year: 2011).

Takami, Yoichiro et al. "Synergistic induction of hepatocyte growth factor in human skin fibroblasts by the inflammatory cytokines interleukin-1 and interferon-γ." Biochemical and Biophysical Research Communications, 327: 212-217, (Year: 2005).

Takeishi, Yasuchika et al. "Importance of Inflammation and Immune Response in Heart Failure—Toll-Like Receptor-Mediated Signaling Pathway and Ventricular Remodeling After Myocardial Infarction." Journal of Clinical and Experimental Medicine, 232(5):378-385, Jan. 30, 2010.

Tamai, Katsuto et al. U.S. Appl. No. 11/997,475, "Mesenchymal Stem Cell Inducer, Tissue Regeneration Promoter and Method of Preparing Mesenchymal Stem Cell." filed Jan. 31, 2008.

Tamai et al., "Nihon Hiuka Gakkai Zasshi," Japanese Journal of Dermatology, 2008, 118(4): 645 (#EL28-4) (translated English abstract attached, titled "New Wave of Wound Healing").

Tamai, K. et al., "PDGFRα-positive cells in bone marrow are mobilized by high mobility group box 1 (HMGB1) to regenerate inured epithelia," Proceedings of the National Academy of Sciences, 108(16): 6609-6614, (Apr. 19, 2011).

Tamai, K. et al., "Development and Outlook of Internal Regeneration-Inducing Pharmaceuticals that use in vivo Bone Marrow Mesenchymal Stem / Progenitor Cell-Mobilizing Factors," Gene & Medicine MOOK, Jul. 22, 2012, pp. 207-212.

Tamai, K., "Development of Regeneration-Inducing Medicine Utilizing Molecular Mechanism for in vivo tissue Regeneration by Circulating Mesenchymal Stem Cells." BIO Clinica, 2016, 31(10): 1042-1046.

Tamai, K. et al., U.S. Appl. No. 17/517,967, "Agents for Promoting Tissue Regeneration by Recruiting Bone Marrow Mesenchymal Stem Cells and/or Pluripotent Stem Cells into Blood ." filed Nov. 3, 2021.

Tamai, K. et al., U.S. Appl. No. 16/768,654, "Therapeutic Agent for Inflammatory Bowel Disease." filed May 30, 2020.

Tamai, Katsuto et al. U.S. Appl. No. 17/995,017, "Peptide having Mesenchymal Stem Cell Mobilizing Activity." filed Sep. 29, 2022.

Tamai, Katsuto et al. U.S. Appl. No. 18/069,421, "Peptide for Inducing Regeneration of Tissue and use Thereof." filed Dec. 21, 2022.

Tamai, Katsuto et al. U.S. Appl. No. 18/152,249, "Pharmaceuticals That Promote Functional Regeneration of Damaged Tissues." filed Jan. 10, 2023.

Tamilselvi, E., et al., "Association of Disease Severity with IL-1 Levels in Methotrexate-Treated Psoriasis Patients." Scandinavian Journal of Immunology, 78: 545-553, (Year: 2013).

Tang, Liping & Eaton, John W. "Fibrin(ogen) Mediates Acute Inflammatory Responses to Biomaterials." J. Exp. Med., 178: 2147-2156, (Year: 1993).

Tang, Daolin et al. "High-Mobility Group Box 1, Oxidative Stress, and Disease." Antioxidants & Redox Signaling, 14(7): 1315-1335, (Year: 2011).

Taniguchi, Noboru et al. "Stage-Specific Secretion of HMGB1 in Cartilage Regulates Endochondral Ossification." Molecular and Cellular Biology, 27(16):5650-5664, (Year:2007).

Tao, Aibin et al. "Cardiomyocyte-Fibroblast Interaction Contributes to Diabetic Cardiomyopathy in Mice: Role of HIMGB1/TLR4/IL-33 Axis." Biochimica et Biophysica Acta, 1852: 2075-2085, (Year: 2015).

Tatsumi, Ryuichi et al. "HGF/SF Is Present in Normal Adult Skeletal Muscle and Is Capable of Activating Satellite Cells," Developmental Biology, 194: 114-128, (Year: 1998).

Telusma, Gloria et al. "Dendritic cell activating peptides induce distinct cytokine profiles," International Immunology, 18(11): 1563-1573, (Year: 2006).

Teoh, N., et al., "Low-Dose TNF-Alpha Protects Against Hepatic Ischemia-Reperfusion Injury in Mice: Implications for Preconditioning." Hepatology, 37(1): 118-128, (Year: 2003).

Thorey, Irmgard S. et al. "The Ca2+ -binding Proteins S100A8 and S100A9 Are Encoded by Novel Injury-regulated Genes*." Journal of Biological Chemistry, 276(38): 35818-35825, (Year: 2009).

Tokuriki, Nobuhiko et al. "Stability Effects of Mutations and Protein Evolvability." Current Opinion in Structural Biology, 19: 596-604, (Year: 2009).

Tsung, Allen et al. "Hepatic Ischemia/Reperfusion Injury Involves Functional TLR4 Signaling in Nonparenchymal Cells." The Journal of Immunology, 175(11): 7661-7668, (Year: 2005).

Türker, Selcan et al. "Nasal route and drug delivery systems." Pharmacy World and Science, 26: 137-142, (Year: 2004).

Uchida et al. "Nihon Seikei Geka Gakkai Zasshi," The Journal of Japanese Orthopaedic Surgical Society, 2005, 79(8): S832, 1-P6-6. (English translation attached, titled "The chemotactic activity of PDGF-bb BMP-2, and FGF-2 towards committed and uncommitted mesenchymal stem cells").

Ueta, Mayumi et al. "Intracellularly Expressed TLR2s and TLR4s Contribution to an Immunosilent Environment at the Ocular Mucosal Epithelium." The Journal of Immunology, 173(5): 3337-3347, (Year: 2004).

Ulloa, Luis et al. "High-mobility group box 1 (HMGB1) protein: Friend and foe," Cytokine & Growth Factor Reviews, 17: 189-201, (Year: 2006).

Uronen-Hansson, Heli et al. "Toll-like Receptor 2 (TLR2) and TLR4 are Present Inside Human Dendritic Cells, Associated with Microtubules and the Golgi Apparatus but are not Detectable on the Cell Surface: Integrity of Microtubules is Required for Interleukin-12 Production in Response to Internalized Bacteria." Immunology, 111: 173-178, (Year: 2004).

User Manual for StemCell Technologies, "Enumeration, Expansion, and Differentiation of Human Mesenchymal Progenitor Cells Using MesenCult." StemCell Technologies, Version 2.2.0, (Year: 2007).

Vandal, Karen et al. "Blockade of S100A8 and S100A9 Suppresses Neutrophil Migration in Response to Lipopolysaccharide." The Journal of Immunology, Sep. 1, 171(5): 2602-2609, (Year: 2003).

Venereau, Emilie et al. "Mutually exclusive redox forms of HMGB1 promote cell recruitment or proinflammatory cytokine release." The Journal of Experimental Medicine, 209(9): 1519-1528, (Year: 2012).

Walfish, Aaron, E. et al. "Crohn Disease (Regional Enteritis; Granulomatou Ileitis; Granulomatous Ileocolitis)." Merck Manual Professional Version, pp. 1-7, (Year: 2020).

Walfish, Aaron, E. et al. "Overview of Inflammatory Bowel Disease," Merck Manual Professional Version, pp. 1-3, (Year: 2020).

Walfish, Aaron, E. et al. "Ulcerative Colitis," Merck Manual Professional Version, pp. 1-8, (Year: 2020).

(56) References Cited

OTHER PUBLICATIONS

Wang, H. et al. "HMG-1 as a Late Mediator of Endotoxin Lethality in Mice," Science, 285(5425): 248-251, (Year: 1999).
Wang, L. et al. "Ischemic cerebral tissue and MCP-1 enhance rat bone marrow stromal cell migration in interface culture," Experimental Hematology, 30: 831-836, (2002).
Wang, H. et al., "Kansaibou no riron to gijutu," Science Press, 5: 58-61 (English translation attached, titled "Theories and Technologies for Stem Cells"), (Year: 2005).
Wang, Haichao et al. "High mobility group protein B1 and the research progress of its biological effect," Journal of Chinese Modern Surgery, 3(22): 1806-1809 (English translation attached), Jul. 9, 1999.
Wang, H. Y., et al. "Rate of Evolution in Brain-Expressed Genes in Humans and Other Primates." PLoS Biol., 5(2): e13, (Year: 2007).
Wang, Y., "Biology of hematopoietic stem cell and the research method therof," Science Press, 1st Edition, pp. 56-58, (Year: 2007).
Wang, W. et al., "Intravenous administration of bone marrow mesenchymal stromal cells is safe for the lung in a chronic myocardial infarction model," Regen Med, 6(2): 179-190, (Year: 2011).
Wang, Fu-Cai et al. "Overexpression of HMGB1 A-box reduced lipopolysaccharide-induced intestinal inflammation via HMGB1/TLR4 signaling in vitro." World J Gastroenterol, 21(25): 7764-7776, Jul. 7, 2015.
Watanabe, Taiji et al. "The Role of HMGB-1 on the Development of Necrosis During Hepatic Ischemia and Hepatic Ischemia/Reperfusion Injury in Mice." Journal of Surgical Research, 124: 59-66, (Year: 2005).
Weintraub, Robert G. et al. "Dilated cardiomyopathy." The Lancet 390.10092:400-414, Feb. 9, 2017.
Wexler, Sarah A. et al., "Adult Bone Marrow is a Rich Source of Human Mesenchymal 'Stem' Cells but Umbilical Cord and Mobilized Adult Blood are Not," British Journal of Haematology, 121(2): 368-374, (Year: 2003).
Whisstock, James C. et al. "Prediction of Protein Function from Protein Sequence and Structure." Quarterly Reviews of Biophysics, 36(3): 307-340, (Year: 2003).
Koç, ON et al. "Mesenchymal Stem Cells: Heading into the Clinic," Bone Marrow Transplantation, 27(3): 235-239, (Year: 2001).
Kohno, T. et al. "High Mobility Group Box 1 Protein is Associated With Post-Infarction Healing Process and Left Ventricular Remodeling." Circ. J., 2008, 72, Supplement 1, p. J-004: 510-511.
Kokkola, R. et al. "RAGE is the Major Receptor for the Proinflammatory Activity of HMGB1 in Rodent Macrophages." Scandinavian Journal of Immunology, 61: 1-9, (Year: 2005).
Komurasaki, Y. et al., "555 Systemic HMGB1 Administration Ameliorated Bleomycin-Induced Skin Fibrosis by Promoting Accumulation of Bone Marrow-Derived Mesenchymal Stem Cells to the Lesion." Journal of Investigative Dermatology, 136(9): S255, (Year: 2016).
Komurasaki, Y., et al., "HMGB1 Ameliorates Bleomycin-Induced Skin Fibrosis by Promoting Accumulation of Mesenchymal Stem Cells to the Lesion." The 48th Annual Meeting of the Japanese Society of Matrix Biology and Medicine, 2016: 78.
Koren-Morag, Nira et al. "White Blood Cell Count and the Incidence of Ischemic Stroke in Coronary Heart Disease Patients." The American Journal of Medicine, 118: 1004-1009, (Year: 2005).
Laflamme, Michael A. et al. "Regenerating the heart," Nature Biotechnology, 23(7): 845-856, Jul. 7, 2005.
Lanza, Robert et al. "Essentials of Stem Cell Biology —Chapter 27, Mesenchymal Stem Cells," Elsevier Academic Press, pp. 205-210, (Year: 2006).
La Rosa, T.J. et al., "Glycine max protein Seq ID No: 211221," Geneseq Accession No. AFQ20044, Oct. 18, 2007.
Lee, Geoffrey et al. "Fully reduced HMGB1 accelerates the regeneration of multiple tissues by transitioning stem cells to Galert." Proceedings of the National Academy of Sciences, 115(19): E4463-E4472, Apr. 19, 2018.
Lemp, Michael A. et al. "The Definition and Classification of Dry Eye Disease: Report of the Definition and Classification Subcommittee of the International Dry Eye Workshop (2007)." The Ocular Surface, 5(2): 75-92, (Year: 2007).
Liao, Dan et al. "Vascular smooth cell proliferation in perfusion culture of porcine carotid arteries." Biochemical and biophysical research communications 372(4): 668-673, Aug. 8, 2008.
Li, S. et al. "Millennium Review, Nonviral gene therapy: promises and challenges," Gene Therapy 7: 31-34, (Year: 2000).
Li, Zihai et al. "Heat-Shock Proteins," Current Protocols in Immunology, Supplement 58, A.IT.1-A.IT.6, (Year: 2003).
Li, Ying et al. "Advancement of Human Multiply, Sex health and Reproductive Medical Science," Peking University Medical Press, Mar. 2007, 1st Edition, pp. 270-271.
Li, Liu-Cheng et al. "Emerging Role of HMGB 1 in Fibrotic Diseases." Journal of Cellular and Molecular Medicine, 18(12): 2331-2339, (Year: 2014).
Limana, Federica et al. "Exogenous High-Mobility Group Box 1 Protein Induces Myocardial Regeneration After Infarction via Enhanced Cardiac C-Kit+ Cell Proliferation and Differentiation," Circulation Research, 97(8): e73-83, (Year: 2005).
Limana, Federica et al. "HMGB1 Attenuates Cardiac Remodelling in the Failing Heart via Enhanced Cardiac Regeneration and miR-206-Mediated Inhibition of TIMP-3." PLoS One, 6(6): e19845, pp. 1-11, Jun. 22, 2011.
Lin, Siang-Yo. et al., "The isolation of novel mesenchymal stromal cell chemotactic factors from the conditioned medium of tumor cells." Experimental Cell Research, 314(17): 3107-3117, (Year: 2008).
Liotta, Francesco et al. "Toll-Like Receptors 3 and 4 Are Expressed by Human Bone Marrow-Derived Mesenchymal Stem Cells and Can Inhibit Their T-Cell Modulatory Activity by Impairing Notch Signaling." Stem Cells, 26(1): 279-289, (Year: 2008).
Liu, Ke-Xin et al. "Human Placental Extract Stimulates Liver Regeneration in Rats," Biological and Pharmaceutical Bulletin, 21(1): 44-49, (Year: 1998).
Lonza BenchGuides_Poietics hMSC Human Mesenchymal Stem Cells and Media (Document # TS-PT-212-7 04/08), 2008, Walkersville, MD, USA.
Lotze, Michael T. "High-mobility group box 1 protein (HMGB1): Nuclear weapon in the immune arsenal." Nature Reviews Immunology 5(4):331-342, (Year: 2005).
Lund, Lars H. et al. "The Registry of the International Society for Heart and Lung Transplantation: Thirty-Third Adult Heart Transplantation Report—2016; Focus Theme: Primary Diagnostic Indications for Transplant." The Journal of Heart and Lung Transplantation, 35(10): 1158-1169, Oct. 1, 2016.
Mansbridge, Jonathan et al. "Skin Tissue Engineering." J. Biomater, Sci. Polymer, Ed., 19(8): 955-968, (Year: 2008).
Maron, Barry J. et al. "Contemporary Definitions and Classification of the Cardiomyopathies—an American Heart Association Scientific Statement from the Council on Clinical Cardiology, Heart Failure and Transplantation Committee Quality of Care and Outcomes Research and Functional Genomics and Translational Biology Interdisciplinary Working Groups; and Council on Epidemiology and Prevention." Circulation, 113: 1807-1816, (Year: 2006).
Martin-Murphy, Brittany V. et al. "The Role of Damage Associated Molecular Pattern Molecules in Acetaminophen-Induced Liver Injury in Mice." Toxicol Lett, 192(3): 1-20, Feb. 15, 2010.
Maruyama, I. "Inflammation and HMGB1/RAGE system." Kekkan Igaku, 2005, 6(5): 519-525 (English translation attached).
Matsumoto, Kunio et al. "Up-Regulation of Hepatocyte Growth Factor Gene Expression by Inerleukin-1 in Human Skin Fibrosis, " Biochemical and Biophysical Research Communications, 188(1): 235-243, Oct. 15, 1992.
Meng, Er-Hong et al. "HMGB1 induces migration of human bone marrow-derived mesenchymal stem cells." Bulletin of the Academy of Military Medical Sciences, 30(3): 213-216 (English translation attached), (Year: 2006).
Meng, Erhong et al. "High Mobility Group Box 1 Protein Inhibits the Proliferation of Human Mesenchymal Stem Cells and Promotes Their Migration and Differentiation along Osteoblastic Pathway." Stem Cells and Development, 17(4):805-814, (Year: 2008).

(56) References Cited

OTHER PUBLICATIONS

Merenmies, Jussi et al. "30-kDa Heparin-binding Protein of Brain (Amphoterin) Involved in Neurite Outgrowth." Journal of Biological Chemistry, 266(25): 16722-16729, Sep. 5, 1991.

Mistry, A.R. et al., "Recombinant HMG1 Protein Produced in Pichia pastoris: A Nonviral Gene Delivery Agent." Biotechniques, 22(4): 718-729, (Year: 1997).

Mori, T. et al., "Stem Cells/ES cells—Mesenchymal Stem Cells—Human Bone Marrow Derived Mesenchymal Stem Cells," Saisei Iryou—Regenerative Medicine, 2005, 4(3): 421-429, 351.

Morikawa, Satoru et al. "Prospective identification, isolation, and systemic transplantation of multipotent mesenchymal stem cells in urine bone marrow." The Journal of Experimental Medicine 206(11):2483-2496, (Year: 2009).

Morosetti, Roberta et al. "MyoD expression restores defective myogenic differentiation of human mesoangioblasts from inclusion-body myositis muscle." PNAS, 103(45): 16995-17000, Nov. 7, 2006.

Mouse care guidance from the Institutional Animal Care and Use Committee at University of California, San Francisco; acuc.ucsf.edu/Policies/BloodCollectionMice.doc; accessed May 15, 2014.

Muhamed, Jaseer et al. "Phenotypic Modulation of Cell Types around Implanted Polyethylene Terephthalate Fabric in Rabbit Muscle." Toxicologic Pathology, 41: 497-507, (Year: 2013).

Muhammad, Sajjad et al. "The HMGB1 Receptor RAGE Mediates Ischemic Brain Damage." The Journal of Neuroscience, 28(46): 12023-12031, Nov. 12, 2008.

Müller, Susanne et al., "The double life of HMGB1 chromatin protein: architectural factor and extracellular signal," EMBO Journal, 20(16): 4337-4340, (Year: 2001).

Musumeci, Domenica et al. "An overview on HMGB1 inhibitors as potential therapeutic agents in HMGB1-related pathologies." Pharmacology & Therapeutics, 141: 347-357, (Year: 2014).

Nakajima et al., "Dynamics and Role of High Mobility Group Box-1 (HMGB-1) in Injured Spinal Cord," Nihon Seikei Geka Gakkai Zasshi (J. Jpn. Orthop. Assoc.), 84(8): S1050, (Year: 2010).

Nakamura, Koji et al. "p38 Mitogen-Activated Protein Kinase Functionally Contributes to Chondrogenesis Induced by Growth/Differentiation Factor-5 in ATDC5 Cells," Experimental Cell Research, 250(2): 351-363, (Year: 1999).

Nakanishi, Shigetada et al., "Membrane Potential-Regulated Ca2+ Signalling in Development and Maturation of Mammalian Cerebellar Granule Cells." J. Physiol., 575(2): 389-395, (Year: 2006).

Narumi, Taro et al. "Abstract 15265: Cardiac-specific Overexpression of High-Mobility Group Box 1 Protects Cardiomyocyte from Apoptosis During the Pathogenesis of Doxorubicin Cardiomyopathy." Circulation, 126:A15265, Mar. 28, 2018.

Narumi, T., et al., "High-mobility Group Box 1 Attenuates Mitochondrial Dysfunction and Apoptosis via Heat Shock Protein Beta 1 Induction in Doxorubicin-induced Cardiomyopathy." Bulletin of Yamagata University (Medical Science), 2015, 33(2): 126-127. http://www.lib.yamagata-u.ac.jp/alllib/elib/kiyou/kiyoum/kiyoum-33-2/image/kiyoum-33-2-125to131.pdf.

Narumi, T., et al., "High-Mobility Group Box 1-Mediated Heat Shock Protein Beta 1 Expression Attenuates Mitochondrial Dysfunction and Apoptosis." Journal of Molecular and Cellular Cardiology, 82: 1-12, (Year: 2015).

NCBI, "Old myocardial infarction." MedGen UID: 57612, retrieved from internet Jan. 19, 2022, <https://www.ncbi.nlm.nih.gov/medgen/57612>.

Nickoloff, Brian J. & Nestle, Frank O. "Recent Insights into the Immunopathogenesis of Psoriasis Provide new Therapeutic Opportunities." J. Clin. Invest., 113(12): 1664-1675, (Year: 2004).

Nojiri, Shunsuke et al. "Synthesized HMGB1 peptide attenuates liver inflammation and suppresses fibrosis in mice." Inflammation and Regeneration 41(28):1-15, (Year: 2021).

WHO Drug Information, vol. 32, No. 1, Appendix 5, p. 155, (Year: 2018).

Wilgus, Tracy A. et al."Neutrophils and wound repair: positive actions and negative reactions." Advances in wound care 2.7: 379-388, (Year: 2013).

Witkowski, Andrzej et al. "Conversion of a β-Ketoacyl Synthase to a Malonyl Decarboxylase by Replacement of the Active-Site Cysteine with Glutamine." Biochemistry, 38: 11643-11650, (Year: 1999).

Wolf, Gunter et al. "From the Periphery of the Glomerular Capillary Wall Toward the Center of Disease." Diabetes, 54(6): 1626-1634, (Year: 2005).

Woodbury, Dale et al. "Adult Rat and Human Bone Marrow Stromal Cells Differentiate into Neurons." Journal of Neuroscience Research, 61(4): 364-370, Aug. 15, 2000.

Wu, Yaojiong et al. "Mesenchymal Stem Cells Enhance Wound Healing Through Differentiation and Angiogenesis," Stem Cells, 25(10): 2648-2659. Epub Jul. 5, 2007.

Wynn, Thomas A. & Ramalingam, Thirumalai R. "Mechanisms of fibrosis: therapeutic translation for fibrotic disease." Nat Med. 18(7): 1028-1040, (Year: 2013).

Yamada, Takayuki et al. "Regulation of osteoclast development by Notch signaling directed to osteoclast precursors and through stromal cells," Blood, 101(6): 2227-2234, (Year: 2003).

Yamaoka, S. et al. "1043 Systemic delivery of HMGB1 peptide ameliorates imiquimod-induced psoriasis-like dermatitis." Journal of Investigative Dermatology, 138(5): S177, (Year: 2018).

Yang, Huan et al. "The many faces of HMGB1: molecular structure-functional activity in inflammation, apoptosis, and chemotaxis." J. Leukoc Biol. 93(6): 865-873, (Year: 2013).

Yang, Huan et al. "Reversing established sepsis with antagonists of endogenous high-mobility group box 1." Proceedings of the National Academy of Sciences, 101(1): 296-301, (Year: 2004).

Yang, Sirui et al. "Does Pretreatment of Bone Marrow Mesenchymal Stem Cells with 5-Azacytidine or Double Intravenous Infusion Improve Their Therapeutic Potential for Dilated Cardiomyopathy?" Medical Science Monitor Basic Research, 19: 20-31, Jan. 14, 2013.

YBOX1_Human, Accession No. P67809, entry version 164, UniProtKB/Swiss-Prot, Sep. 12, 2018.

Youn, Ju Ho et al. "High Mobility Group Box 1 Protein Binding to Lipopolysaccharide Facilitates Transfer of Lipopolysaccharide to CD14 and Enhances Lipoplysaccharide-Mediated TNF-α Production in Human Monocytes," Journal of Immunology, 180(7): 5067-5074, (Year: 2008).

Yuan, Y. et al. "Differentiation of Mesenchymal Stem Cells in Cardiomyogenic Cells Under the Induction of Myocardial Cell Lysate." Chinese Journal of Cardiology, 33(2): 170-173, (Year: 2005).

Yu, Q. et al. "Impact of Repeated Intravenous Bone Marrow Mesenchymal Stem Cells Infusion on Myocardial Collagen Network Remodeling in a Rat Model of Doxorubicin-Induced Dilated Cardiomyopathy." Molecular and Cellular Biochemistry, 2014: 279-285, (Year: 2014).

Zheng, Xiaoyan et al. "Adeno-associated virus-mediated colonic secretory expression of HMGB1 A box attenuates experimental colitis in mice." J Gene Med, 18(10): 261-272, (Year: 2016).

Zhao, Ji & Jiang, Hong "The Study Progression of the Role of HMGBI in Ichemic Heart Failure." MOlecular Cardiology of China, pp. 1169-1171, Dec. 25, 2014.

Zhou, X., et al., "Section 2 The translation process of genetic information." Molecular Genetics, 1992, pp. 141-143.

Zhou, Xiaoya et al. "Exogenous High-Mobility Group Box 1 Protein Injection Improves Cardiac Function after Myocardial Infarction: Involvement of Wnt Signaling Activation," Journal of Biomedicine and Biotechnology, vol. 2012, pp. 1-5, (Year: 2012).

Zhou, Yan-Hong et al. "High mobility group box 1 protein attenuates myocardial ischemia reperfusion injury via inhibition of the p38 mitogen-activated protein kinase signaling pathway." Experimental and Therapeutic Medicine, 14: 1582-1588, (Year: 2017).

Baer, Patrick C. et al. "Comprehensive Phenotypic Characterization of Human Adipose-Derived Stromal/Stem Cells and Their Subsets by a High Throughput Technology." Stem Cells and Development 00(00):1-10, (Year: 2012).

(56) References Cited

OTHER PUBLICATIONS

Bigazzi, Pierluigi E. & Rose, Noel R. "Introduction to Review Series on Animal Models of Human Disease." Clinical Immunology and Immunopathology, 74(1): 1, (Year: 1995).

Bretag, Allan "Too much hype, not enough hope: Are balanced reporting and proper controls too much to expect from therapeutic studies in animal models of neuromuscular diseases that presage clinical trials in humans?" Neuromuscular Disorders 17:203-205 (Year: 2007).

He, Yiyu et al. "Exogenous High-Mobility Group Box 1 Protein Prevents Postinfarction Adverse Myocardial Remodeling Through TGF-β/Smad Signaling Pathway." Journal of Cellular Biochemistry 114: 1634-1641, (Year: 2013).

PROCR gene—Protein C Receptor. Downloaded from https://www.genecards.org/cgi-bin/carddisp.pl?gene=PROCR, accessed Mar. 31, 2023.

Ahrens, Norbert et al. "Mesenchymal Stem Cell Content of Human Vertebral Bone Marrow." Transplantation 78(6): 925-929, (Year: 2004).

Aikawa, Eriko et al. "HMGB1 accelerates skin regeneration by inducing bone marrow mesenchymal stromal cells." Journal of Dermatological Science 84(1): 1-14, (Year: 2016).

Alden, T. D., et al. "In Vivo Endochondral Bone Formation Using a Bone Morphogenetic Protein 2 Adenoviral Vector." Human Gene Therapy, Sep. 1999, 10(13): 2245-2253.

Andersson, Ulf et al. "HMGB1 is a Therapeutic Target for Sterile Inflammation and Infection." Annu Rev Immunol. 29: 139-162 (Year: 2011).

Andersson, Ulf et al., "HMGB1 as a DNA-binding cytokine." Journal of Leukocyte Biology, 72: 1084-1091, (Year: 2002).

Andrassy, Martin et al. "High-Mobility Group Box-1 in Ischemia-Reperfusion Injury of the Heart." Circulation 117(25): 3216-3226, (Year: 2008).

Arminan, A. et al., "Mesenchymal Stem Cells Provide Better Results Than Hematopoietic Precursors for the Treatment of Myocardial Infarction." Journal of the American College of Cardiology, 55(20): 2244-2253, (Year: 2010).

Arnau, J. et al., "Current Strategies for the use of Affinity Tags and Tag Removal for the Purification of Recombinant Proteins." Protein Expression and Purification, 48: 1-13, (Year: 2006).

Asch, F.M. et al. "Lack of sensitivity of the electrocardiogram for detection of old myocardial infarction: A cardiac magnetic resonance imaging study." American Heart Journal, 152(4): 742-748, (Year: 2006).

Ball, S.G., et al., "Mesenchymal stem cells and neovascularization: role of platelet-derived growth factor receptors." J. Cell. Mo. Med., 11(5): 1012-1030, (Year: 2007).

Basso, D. M. et al., "Basso Mouse Scale for Locomotion Detects Differences in Recovery after Spinal Cord Injury in Five Common Mouse Strains." Journal of Neurotrauma, 23(5): 635-659, (Year: 2006).

Berry, M. F. et al., "Mesenchymal stem cell injection after myocardial infarction improves myocardial compliance." Am. J. Physiol. Heart Circ. Physiol. 290(6): H2196-H2203, Feb. 10, 2006.

Bhattacharya, Roshni et al. "Impact of genetic variation on three dimensional structure and function of proteins." PloS one, 12(3): 1-22, Mar. 15, 2017.

Bianchi, M. E., "High mobility group 1 protein (HMGB1) N-terminal peptide." Geneseq Accession No. ADO80180, Aug. 12, 2004.

Bianchi, M. E. et al., "The DNA binding site of HMG1 protein is composed of two similar segments (HMG boxes), both of which have counterparts in other eukaryotic regulatory proteins." The EMBO Journal, 11(3):1055-1063, (Year: 1992).

Bittira, B. et al., "Mobilization and homing of bone marrow stromal cells in myocardial infarction." European Journal of Cardio-thoracic Surgery, 24(3): 393-398, (Year: 2003).

Blain, Alison M. & Straub, Volker W. "δ-Sarcoglycan-deficient muscular dystrophy: from discovery to therapeutic approaches." Skeletal Muscle, 1(13): 1-12, (Year: 2011).

Brunner, S., et al., "Erythropoietin Administration After Myocardial Infarction in Mice Attenuates Ischemic Cardiomyopathy Associated with Enhanced Homing of Bone Marrow-Derived Progenitor Cells Via the CXCR-4/SDF-1 Axis." The FASEB Journal, 23: 351-361, (Year: 2009).

BTF3_Human, Accession No. P20290, entry version 166, UniProtKB/Swiss-Prot, Sep. 12, 2018.

Bustin, Michael "Regulation of DNA-Dependent Activities by the Functional Motifs of the High-Mobility-Group Chromosomal Proteins." Mol. Cell. Biol., 19(8): 5237-5246, (Year: 1999).

Cairo, Mitchell. S. "Results of a Phase I/II Trial of Recombinant Human Granulocyte-Macrophage Colony-Stimulating Factor in Very Low Birthweight Neonates: Significant Induction of Circulatory Neutrophils, Monocytes, Platelets, and Bone Marrow Neutrophils." Blood, 86(7): 2509-2515, (Year: 1995).

"Cardiomegaly" Merriam Webster, 2015 archived page, accessed via Wayback Machine [online] [accessed at https://web.archive.org/web/20150107154504/https://www.merriam-webster.com/medical/cardiomegaly on May 21, 2020]. (Year: 2015).

"Cardiomyopathy: Symptoms, diagnosis and treatment." Harvard Health Publishing Harvard Medical School, Dec. 29, 2014.

Castro, Raymond. F. et al., "Failure of Bone Marrow Cells to Transdifferentiate into Neural Cells in Vivo." Science, 297(5585): 1299, Aug. 23, 2002.

Chamberlain, Giselle. et al., "Concise Review: Mesenchymal Stem Cells: Their Phenotype, Differentiation Capacity, Immunological Features, and Potential for Homing." Stem Cells, 25: 2739-2749, Jul. 26, 2007.

Chan, James. K., et al. "Alarmins: awaiting a clinical response." The Journal of Clinical Investigation 122(8):2711-2719, (Year: 2012).

Charoonpatrapong, Kanokwan et al., "HMGB1 Expression and Release by Bone Cells." Journal of Cellular Physiology, 207(2): 480-490, (Year: 2006).

Chen, Xiaoguang et al., "Human Bone Marrow Stromal Cell Cultures Conditioned by Traumatic Brain Tissue Extracts: Growth Factor Production." Journal of Neuroscience Research, 69: 687-691, (Year 2002).

Chen, Y. et al., "Coaxing bone marrow stromal mesenchymal stem cells towards neuronal differentiation: progress and uncertainties." Cellular and Molecular Life Sciences, 63(14): 1649-1657, (Year: 2006).

Chen, Tao, et al., "Involvement of high mobility group box-1 in imiquimod-induced psoriasis-like mice model." Journal of Dermatology, 44: 573-581, (Year: 2017).

Chopp, Michael, & Li, Yi., "Treatment of neural injury with marrow stromal cells." The Lancet Neurology, 1(2):92-100, (Year: 2002).

Chou, Denise. K. H. et al., "Identity of nuclear high-mobility-group protein, HMG-1, and sulfoglucuronyl carbohydrate-binding protein, SBP-1, in brain." Journal of Neurochemistry, 77(1): 120-131, (Year: 2001).

Cole, J.S.III, "Pharmacologic Mobilization of Mesenchymal Stem Cells for Enhanced Bone Formation." Colby College, Rush University, 2009, Thesis, UMI No. 1466383, 1-82.

Degryse, B. et al., "The High Mobility Group (HMG) Boxes of the Nuclear Protein HMG1 Induce Chemotaxis and Cytoskeleton Reorganization in Rat Smooth Muscle Cells." The Journal of Cell Biology, 152(6):1197-1206, Mar. 19, 2001.

Delarosa, Olga., & Lombardo, Eleuterio "Modulation of Adult Mesenchymal Stem Cells Activity by Toll-Like Receptors: Implications on Therapeutic Potential." Mediators of Inflammation, vol. 2010, Article ID: 865601, pp. 1-9, (Year: 2010).

Del Buono, Marco Giuseppe et al. "Ischemic Cardiomyopathy and Heart Failure After Acute Myocardial Infarction." Current Cardiology Reports, 24(10):1505-1515, Aug. 16, 2022.

Desai, N. P. & Hubbell, J. A., "Tissue response to intraperitoneal implants of polyethylene oxide-modified polyethylene terephthalate." Biomaterials, 13(8): 505-510 (Year: 1992).

Desantis, S. et al., "TNFα Deficiency Results in Increased IL-18 in an Early Onset of Spontaneous Murine Colitis." Cell Death and Disease, 8: e2993, pp. 1-7, (Year: 2017).

De Souza, A.W.S. et al., "HMGB1 in vascular diseases: its role in vascular inflammation and atherosclerosis." Autoimmunity Reviews, 1: 909-917, (Year: 2012).

(56) References Cited

OTHER PUBLICATIONS

Dong, Y. et al., "HMGB1 Protein Does Not Mediate the Inflammatory Response in Spontaneous Spinal Cord Regeneration." The Journal of Biological Chemistry, 288(25): 18204-18218, Jun. 11, 2013.

Eckert, R.L. et al., "S100 Proteins in the Epidermis." The Journal of Investigative Dermatology, 123(1): 23-33, (Year: 2004).

Ehrchen, Jan M. et al., "The endogenous Toll-like receptor 4 agonist S100A8/S100A9 (calprotectin) as innate amplifier of infection, autoimmunity, and cancer." Journal of Leukocyte Biology, 86: 557-566, (Year: 2009).

Erlandsson, H. et al., "The nuclear protein HMGB1 as a proinflammatory mediator," European Journal of Immunology, 34(6): 1503-1512, (Year: 2004).

Esposito, Emanuela. et al., "Melatonin reduces stress-activated/mitogen-activated protein kinases in spinal cord injury." J. Pineal. Res., 46: 79-86, (Year: 2009).

Fang, Ping et al. "HMGB1 Contributes to Regeneration After Spinal Cord Injury in Adult Zebrafish." Mol. Neurobio., 49: 472-483, (Year: 2014).

Fenton, Aron W. et al. "Rheostat positions: a new classification of protein positions relevant to pharmacogenomics." Medicinal Chemistry Research 29:1133-1146, (Year: 2020).

Forte, Giancarlo et al., "Hepatocyte Growth Factor Effects on Mesenchymal Stem Cells: Proliferation, Migration, and Differentiation." Stem Cells, 24: 23-33 (Year: 2006).

Frankel, Arthur E. et al., "Characterization of Diphtheria Fusion Proteins Targeted to the Human Interleukin-3 Receptor." Protein Engineering, 13(8): 575-581, (Year: 2000).

Freitag, Julien et al. "The effect of autologous adipose derived mesenchymal stem cell therapy in the treatment of a large osteochondral defect of the knee following unsuccessful surgical intervention of osteochondritis dissecans—a case study." BMC Musculoskeletal Disorders 18(298):1-11, (Year: 2017).

Fritsch, Anja., et al., "A Hypomorphic Mouse Model of Dystrophic Epidermolysis Bullosa Reveals Mechanisms of Disease and Response to Fibroblast Therapy." The Journal of Clinical Investigation, 118(5): 1669-1679, (Year: 2008).

NPM_Human, Accession No. P06748, entry version 164, UniProtKB/Swiss-Prot, Sep. 12, 2018.

O'Callaghan, A., et al., "HMGB1 as a Key Mediator of Tissue Response to Injury: Roles in Inflammation and Tissue Repair." European Surgery, 38: 283-292, (Year: 2006).

Opitz, Christiane A. et al. "Toll-Like Receptor Engagement Enhances the Immunosuppressive Properties of Human Bone Marrow-Derived Mesenchymal Stem Cells by Inducing Indoleamine-2, 3-dioxygenase-1 via Interferon-β and Protein Kinase R," Stem Cells, 27(4): 909-919, (Year: 2009).

Otsuru, S. et al., "BMP-2 mobilizes robust bone marrow mesenchymal progenitor cells to the circulating blood in pone regeneration," The 28th Meeting of the Molecular Biology Society of Japan, 2005, 733(3P-1012) (translated English abstract attached).

Ozaki, Yoshie et al., "Comprehensive Analysis of Chemotactic Factors for Bone Marrow Mesenchymal Stem Cells," Stem Cells and Development, 16(1): 119-129, (Year: 2007).

PA2G4_Human, Accession No. Q9UQ80, entry version 189, UniProtKB/Swiss-Prot, Sep. 12, 2018.

Palumbo, Roberta et al. "Extracellular HMGB1, a signal of tissue damage, induces mesoangioblast migration and proliferation," The Journal of Cell Biology, 164(3): 441-449, (Year: 2004).

Palumbo, R. et al., "High mobility group box 1 protein, a cue for stem cell recruitment," Biochemical Pharmacology, 68(6): 1165-1170, (Year: 2004).

Palumbo, R. et al., "Cells migrating to sites of tissue damage in response to the danger signal HMGB1 require NF-κB activation," Journal of Cell Biology, 179(1): 33-40, (Year: 2007).

Pandya, Nilesh M. et al. "Angiogenesis—A New Target for Future Therapy." Vascular Pharmacology, 44: 265-274, (Year: 2006).

Panepucci, Rodrigo A. et al. "Abstract # 4427: Comparison of Gene Expression of Mesenchymal Stem Cells from the Umbilical Cord and from the Bone Marrow," Blood, 16(102): Abstract, (Year: 2003).

Panepucci, Rodrigo A. et al. "Comparison of Gene Expression of Umbilical Cord Vein and Bone Marrow-Derived Mesenchymal Stem Cells." Stem Cells, 22(7): 1263-1278, (Year: 2004).

Pankov, Roumen et al. "Fibronectin at a glance." J. Cell Sci., 115(20): 3861-3863, (Year: 2002).

Park, Jong Sung et al. "Involvement of Toll-Like Receptors 2 and 4 in Cellular Activation by High Mobility Group Box 1 Protein." Journal of Biological Chemistry, 279(9): 7370-7377, (Year: 2004).

Paul, S.R. et al., "Stromal Cell-Associated Hematopoiesis: Immortalization and Characterization of a Primate Bone Marrow-Derived Stromal Cell Line." Blood, 77(8): 1723-1733, (Year: 1991).

Pevsner-Fischer, Meirav et al. "Toll-like receptors and their ligands control mesenchymal stem cell functions." Blood, 109(4): 1422-1432, (Year: 2007).

PFD5_Human, Accession No. Q99471, entry version 167, UniProtKB/Swiss-Prot, Sep. 12, 2018.

Pittenger, Mark F. et al. "Multilineage Potential of Adult Human Mesenchymal Stem Cells." Science, 284(5411): 143-147, (Year: 1999).

Popovic, Karin et al. "Increased Expression of the Novel Proinflammatory Cytokine High Mobility Group Box Chromosomal Protein 1 in Skin Lesions of Patients With Lupus Erythematosus." Arthritis & Rheumatism, 52(11): 3639-3645, (Year: 2005).

PRS6A_Human, Accession No. P17980, entry version 204, UniProtKB/Swiss-Prot, Sep. 12, 2018.

Pusterla, Tobias et al. "High mobility group B2 is secreted by myeloid cells and has mitogenic and chemoattractant activities similar to high mobility group B1." Autoimmunity, 2009, 42(4): 308-310.

Quertainmont, Renaud et al. "Mesenchymal Stem Cell Graft Improves Recovery after Spinal Cord Injury in Adult Rats through Neurotrophic and Pro-Angiogenic Actions." PLoS One, 7(6): 1-15, e39500, (Year: 2012).

Racanelli, Vito et al., "The Liver as an Immunological Organ." Hepatology, 43(2): Suppl. 1—S54-S62, (Year: 2006).

Rahimi-Movaghar, Vafa et al. "Effect of Decompression on Complete Spinal Cord Injury in Rats," International Journal of Neuroscience, 118: 1359-1373, (Year: 2008).

Raicevic, Gordana et al. "Inflammation modifies the pattern and the function of Toll-like receptors expressed by human mesenchymal stromal cells," Human Immunology, 71(3): 235-244, (Year: 2010).

Raucci, Angela et al. "The Janus Face of HMGB1 in Heart Disease: A Necessary Update." Cellular and Molecular Life Sciences, 76: 211-229, (Year: 2019).

Robinson, Matthew J. et al. "The S100 Family Heterodimer, MRP-8/14, Binds with High Affinity to Heparin and Heparan Sulfate Glycosaminoglycans on Endothelial Cells." Journal of Biological Chemistry, 277(5): 3658-3665, (Year: 2002).

Ross, Michael H. et al. "Histology: a Text and Atlas: With Correlated Cell and Molecular Biology." Lippincott Williams & Wilkins, 2018.

Ryckman, Carle et al. "Proinflammatory Activities of S100: Proteins S100A8, S100A9, and S100A8/A9 Induce Neutrophil Chemotaxis and Adhesion." J. Immunol., 170(6): 3233-3242, (Year: 2003).

Santamaria-Kisiel, Liliana et al. "Calcium-dependent and -independent interactions of the S100 protein family." Biochem. J., 396: 201-214, (Year: 2006).

Sasaki, Mikako et al. "Mesenchymal Stem Cells Are Recruited into Wounded Skin and Contribute to Wound Repair by Transdifferentiation into Multiple Skin Cell Type." The Journal of Immunology, 180(4): 2581-2587, Feb. 15, 2008.

Saver, Jeffrey L. "Time Is Brain-Quantified." Stroke, 37: 263-266, Jan. 2006.

Schaffer, Michael R. et al. "Wound Fluid Inhibits Wound Fibroblast Nitric Oxide Synthesis." Journal of Surgical Research, 122(1): 43-48, (Year: 2004).

Schon, Michael P. & Boehncke, W. Henning "Medical Progress: Psoriasis." The New England Journal of Medicine, 352(18): 1899-1912, (Year: 2005).

(56) References Cited

OTHER PUBLICATIONS

Scoote, Mark et al. "Chapter 19—Pathophysiology of Heart Failure." Essential Cardiology: Principles and Practice, 2nd Edition, Chapter 19, pp. 347-369, (Year: 2006).
Seffernick, J. L., "Melamine Deaminase and Atrazine Chlorohydrolase: 98 Percent Identical but Functionally Different." Journal of Bacteriology, 183(8): 2405-2410, (Year: 2001).
Selected cardiac diagnoses and ICD-10 codes, 2021, 1 page.
Seong, Seung-Yong & Matzinger, Polly "Hydrophobicity: an ancient damage-associated molecular pattern that initiates innate immune responses." Nature Reviews: Immunology, 4(6): 469-478, (2004).
Shibata, Futoshi et al. "Fibroblast growth-stimulating activity of S100A9 (MRP-14)." Eur. J. Biochem., 271(11): 2137-2143, (Year: 2004).
Shing, Y. et al., "Heparin Affinity: Purification of a Tumor-Derived Capillary Endothelial Cell Growth Factor." Science, 223: 1296-1299, Mar. 23, 1984.
Sidney, Laura E. "Concise Review: Evidence for CD34 as a Common Marker for Diverse Progenitors." Stem Cells 32(6):1380-1389, Feb. 4, 2014.
Simard, Alain R. et al. "Bone Marrow-Derived Microglia Play a Critical Role in Restricting Senile Plaque Formation in Alzheimer's Disease." Neuron, 49(4): 489-502, (Year. 2006).
Sisakian, H. S. et al. "Dilated Cardiomyopathy: Evoltion of Pathogenesis Concepts and Potential for New Therapies." New Armenian Medical Journal 9(1):4-18, (Year: 2015).
Slater, M. et al. "Endometriotic cells exhibit metaplastic change and oxidative DNA damage as well as decreased function, compared to normal endometrium." Journal of Molecular Histology, 36(4): 257-263, (Year: 2005).
Somia, Nikunj & Verma, Inder M. "Gene Therapy: Trials and Tribulations." Nature Reviews: Genetics, 1(2): 91-99, Nov. 2000.
Soo, Eliza T. L. et al. "Heat Shock Proteins as Novel Therapeutic Targets in Cancer." in vivo, 22(3): 311-315, (Year: 2008).
SP16H_Human, Accession No. Q9Y5B9, entry version 157, UniProtKB/Swiss-Prot, Sep. 12, 2018.
Straino, Stefania et al. "High-Mobility Group Box 1 Protein in Human and Murine Skin: Involvement in Wound Healing." Journal of Investigative Dermatology, 128: 1545-1553, (Year: 2008).
Suchacki, Karla J. "Bone marrow adipose tissue: formation, function and regulation." Current opinion in PHarmacology 28:50-56, (Year: 2016).
Sun, Shengkun et al. "Isolation of Mouse Marrow Mesenchymal Progenitors by a Novel and Reliable Method." Stem Cells, 21(5): 527-535, (Year: 2003).
Alshorafa, A. K.H., et al., "Psoriasis Is Associated with Low Serum Levels of Hydrogen Sulfide, a Potential Anti-inflammatory Molecule." The Tohoku Journal of Experimental Medicine, 228.4 (2012): 325-332.
Charles River Laboratories Ineternational, Inc., Research Models, C57BL/6 Mice, Nomenclature: C57BL/6NCrl, 2019. Retrieved from: https://www.criver.com/sites/default/files/resources/doc_a/C57BL6MouseModelInformationSheet.pdf, pp. 1-6.
ICH GCP, US Clinical Trials Registry, Clinical Trial NCT01287897, A Study to Assess the Efficacy and Safety of PF-04236921 in Subjects with Crohn's Disease who Failed Anti-TNF Therapy (Andante), <<accessed from the Internet Dec. 1, 2023, https://ichgcp.net/clinical-trials-registry/NCT01287897>>.
Danese, S., et al., "Randomised trial and open-label extension study of an anti-interleukin-6 antibody in Crohn's disease (Andante I and II)." Gut, 2019, 68(1): 40-48.
De Meyer, S.F., et al., "Extracellular Chromatin Is an Important Mediator of Ischemic Stroke in Mice." Arterioscler Thromb Vasc Biol, 2012, 32: 1884-1891.
Drumm, M.L., et al., "Genetic Variation and Clinical Heterogeneity in Cystic Fibrosis." Annu Rev Pathol Mech Dis, 2012, 7: 267-282.
Focosi, D., et al., "Conditioning response to granulocyte colony-stimulating factor via the dipeptidyl peptidase IV-adenosine deaminase complex." Journal of Leucocyte Biology, 84.2 (2008): 331-337.
Goodman, W. A., et al., "IL-6 Signaling in Psoriasis Prevents Immune Suppression by Regulatory T Cells." The Journal of Immunology, 183.5 (2009): 3170-3176.
Grossman, R. M., et al., "Interleukin 6 is expressed in high levels in psoriatic skin and stimulates proliferation of cultured human keratinocytes." Proceedings of the National Academy of Sciences, 86.16 (1989): 6367-6371.
Hinderer, S., et al., "Cardiac fibrosis—A short review of causes and therapeutic strategies." Advanced drug delivery reviews, 146 (2019): 77-82.
Ito, H., et al., "A Pilot Randomized Trial of a Human Anti-Interleukin-6 Receptor Monoclonal Antibody in Active Crohn's Disease." Gastroenterology, 2004, 126(4): 989-996.
Ko, E., et al., "SERPINA3 is a key modulator of HNRNP-K transcriptional activity against oxidative stress in HCC." Redox Biology, 2019, 24(101217): 1-10.
Kolundzic, E., et al., "FACT Sets a Barrier for Cell Fate Reprogramming in Caenorhabditis elegans and Human Cells." Developmental Cell, 2018, 46: 611-626, e1-e12.
Kwak, M. S., et al., "Immunological Significance of HMGB1 Post-Translational Modification and Redox Biology." Frontiers in immunology, 11 (2020): 1189, 1-16.
Lee, S.-A., et al., "The Role of High Mobility Group Box 1 in Innate Immunity." Yonsei Medical Journal, 55.5 (2014): 1165-1176.
Leenaars, M., et al., "Critical Steps in the Production of Polyclonal and Monoclonal Antibodies: Evaluation and Recommendations." ILAR Journal, 2005, 46(3): 269-279.
Li, D. C. J., "Research progress on the mechanism and induction methods for the differentiation of mesenchymal stem cells." Infect Inflamm Rep, vol. 12, No. 1, Mar. 2011: 62-64.
Nam, Y.-S., et al., "Negative impact of bone-marrow-derived mesenchymal stem cells on dextran sulfate sodium-induced colitis." World Journal of Gastroenterology, 2015, 21(7): 2030-2039.
Neuner, P., et al., "Increased IL-6 Production by Monocytes and Keratinocytes in Patients with Psoriasis." Journal of Investigative Dermatology, 97.1 (1991): 27-33.
Di Paola, R., et al. "S-Acetyl-Glutathione Attenuates Carbon Tetrachloride-Induced Liver Injury by Modulating Oxidative Imbalance and Inflammation." International journal of molecular sciences, 23.8 (2022): 4429, 1-16.
Scholten, D., et al., "The carbon tetrachloride model in mice." Laboratory Aanimals, 2015, 49(S1): 4-11.
Shedoeva, A., et al., "Wound Healing and the Use of Medicinal Plants." Evidence-Based Complementary and Alternative Medicine, 2019.1 (2019): 2684108, 1-30.
Shi, D., et al., "Nucleocapsid Interacts with NPM1 and Protects it from Proteolytic Cleavage, Enhancing Cell Survival, and is Involved in PEDV Growth." Scientific Reports, 2017, 7(39700): pp. 1-16.
Shirley, D., et al., "Systemic recruitment of osteoblastic cells in fracture healing." Journal of Orthopaedic Research, 2005, 23: 1013-1021.
Six, I., et al., "Beneficial effect of pharmacological mobilization of bone marrow in experimental cerebral ischemia." European Journal of Pharmacology, 2003, 458: 327-328.
Sommer, J., et al., "Interleukin-6, but not the interleukin-6 receptor plays a role in recovery from dextran sodium sulfate-induced colitis." International Journal of Molecular Medicine, 2014, 34(3): 651-660.
SPT16 (D712K) Rabbit Monoclonal Antibody, from https://www.cellsignal.com/products/primary-antibodies/spt16-d7i2krabbit-mab/12191?N=572536551+4294956287&Nrpp=100&No=%7Boffset%7D&fromPage=plp, pp. 1-5, accessed Nov. 1, 2023.
Tamai, K., "Experimental result demonstrating that the 1-44 peptide is not an antagonist of the HMGB1 protein unlike A box." Jul. 28, 2023, pp. 1-2, submitted on Nov. 13, 2023 in EP 3607963.
Tamai, K., et al., "179 Systemic administration of HMGB1 peptide drastically improves survival of the RDEB model mice by mobilizing multipotent stem/progenitor cells from bone marrow", Journal of Investigative Dermatology, vol. 137, No. 10, Supplement 2, 2017: S223.
Tamai, K., et al. U.S. Appl. No. 18/776,908, " Disease Treatment Drug Based on Mesenchymal-Stem-Cell Mobilization." filed Jul. 18, 2024, pp. 1-53.

(56) References Cited

OTHER PUBLICATIONS

Yampolsky, L.Y., et al., "The Exchangeability of Amino Acids in Proteins." Genetics, 2005, 170(4): 1459-1472.

Yang, D., et al., "High mobility group box-1 protein induces the migration and activation of human dendritic cells and acts as an alarmin." Journal of Leucocyte Biology, 81.1 (2007): 59-66.

Yang, Y.-H. K., et al., "Changes in phenotype and differentiation potential of human mesenchymal stem cells aging in vitro." Stem Cell Research & Therapy, 2018, 9(131): 1-14.

Younis, S., et al., "Tumor Necrosis Factor-associated Palmoplantar Pustular Psoriasis Treated with Interleukin 6 Blocker." The Journal of Rheumatology, 39.10 (2012): 2055-2056.

Zandarashvili, L., et al., "Real-time Kinetics of High-mobility Group Box 1 (HMGB1) Oxidation in Extracellular Fluids Studied by in Situ Protein NMR Spectroscopy." Journal of Biological Chemistry, 288.17 (2013): 11621-11627.

Aikawa, E., et al., "Systemic high-mobility group box 1 administration suppresses skin inflammation by inducing an accumulation of PDGFRα+ mesenchymal cells from bone marrow." Scientific Reports, 2015, 5(11008), pp. 1-14.

Britannica, the Editors of Encyclopaedia. "peptide". Encyclopedia Britannica, Sep. 9, 2024, https://www.britannica.com/science/peptide. Accessed Sep. 18, 2024.

Kawada, H., et al., "Nonhematopoietic mesenchymal stem cells can be mobilized and differentiate into cardiomyocytes after myocardial infarction." Blood, Dec. 2004, 104(12): 3581-3587.

Nishimura, Y.I., et al., "No. 9 Establishment of canine liver fibrosis model and evaluation of the efficacy of cultured autologous bone marrow-derived mesenchymal stem cell infusion." Yamaguchi Medical Journal, 2016, 65(4): p. 196.

Tamai, K., "Declaration of Katsuto Tamai, M.D., Ph.D. Under 37 C.F.R. §1.132." Sep. 7, 2022, pp. 1-13, submitted Sep. 16, 2022 in U.S. Appl. No. 16/499,604.

Ukai, R., et al., "Mesenchymal Stem Cells Derived from Peripheral Blood Protects against Ischemia." Journal of Neurotrauma, 2007, 24(3): 508-520.

Andersson, U., et al., "The role of HMGB1 in the pathogenesis of rheumatic disease." Biochimica et Biophysica Acta, 2010, 1799: 141-148.

Dieleman, L.A., et al., "Dextran Sulfate Sodium-Induced Colitis Occurs in Severe Combined Immunodeficient Mice." Gastroenterology, 1994, 107(6): 1643-1652.

Silva, I., et al., "Preclinical Study in Vivo for New Pharmacological Approaches in Inflammatory Bowel Disease: A Systematic Review of Chronic Model of TNBS-Induced Colitis." Journal of Clinical Medicine, 2019, 8(10), 1574, pp. 1-20.

Štros, M., "HMGB proteins: Interactions with DNA and chromatin." Biochimica et Biophysica Acta, 2010, 1799: 101-113.

\* cited by examiner

THERAPEUTIC AGENT FOR PSORIASIS

CROSS REFERENCE TO RELATED APPLICATIONS

This application is a continuation of U.S. patent application Ser. No. 16/967,919, filed Aug. 6, 2020; which is a National Stage Application of International Application Number PCT/JP2019/004330, filed Feb. 7, 2019; which claims priority to Japanese Application No. 2018-020687, filed Feb. 8, 2018.

The Sequence Listing for this application is labeled "SeqList-03Aug22.xml", which was created on Aug. 3, 2022, and is 5 KB. The entire content is incorporated herein by reference in its entirety.

TECHNICAL FIELD

The present application relates to pharmaceutical compositions for the prevention and/or treatment of psoriasis, which comprise a fragment peptide of the high mobility group box 1 (HMGB1) protein.

BACKGROUND ART

Psoriasis is a chronic skin disease characterized by inflammation of the skin and abnormal proliferation of keratinocytes. Although the cause of psoriasis is not yet fully elucidated, the disease is thought to develop by genetic factors plus various external factors (infectious diseases, stress, drugs, etc.). In recent years, it has been shown that abnormalities in immune function are involved.

For the treatment of psoriasis, corticosteroids, vitamin D3 derivatives, immunosuppressants (such as cyclosporin), vitamin A derivatives (retinoids), biological preparations (e.g., anti-TNF-α antibodies, anti-IL-17A antibodies, and anti-IL-17 receptor A antibodies), and such have been used; however, there are cases where sufficient effect cannot be obtained. Furthermore, in terms of side effects, there is room for improvement since the following problems and such exist: skin atrophy and capillary dilatation caused by long-term use of corticosteroid preparations; increased blood calcium level (and resulting fatigue, weakness, loss of appetite, etc.) caused by vitamin D3 derivatives; renal dysfunction, hepatic dysfunction, leukopenia, and increased blood pressure caused by immunosuppressants; and teratogenicity by vitamin A derivatives. Therefore, development of a more effective and safer therapeutic agent for psoriasis, the type of which is different from existing therapeutic agents, is desired.

CITATION LIST

Patent Literature

[PTL 1] WO2012/147470
[PTL 2] WO2014/065347
[PTL 3] WO2014/065348

SUMMARY OF INVENTION

Technical Problem

An objective of the present application is to provide novel pharmaceuticals that are effective in the treatment of psoriasis.

Solution to Problem

As a result of searching for substances effective in the treatment of psoriasis, the present inventors discovered that an HMGB1 fragment peptide having a specific amino acid sequence exhibits an effect of suppressing erythema, scaling (desquamation), and thickening (infiltration) of the skin in an animal model of psoriasis. Accordingly, the present application provides pharmaceutical compositions for the prevention and/or treatment of psoriasis, which comprise the specific HMGB1 fragment peptide.

Namely, the present application provides the following:
[1]
A pharmaceutical composition for the prevention and/or treatment of psoriasis, comprising a substance described in any of the following (a) to (c) (herein below referred to as substance A):
 (a) an HMGB1 fragment peptide comprising the amino acid sequence described in SEQ ID NO: 1;
 (b) a peptide comprising an amino acid sequence in which one or more amino acids are substituted, deleted, inserted, or added in the amino acid sequence described in SEQ ID NO: 1; and
 (c) a peptide comprising an amino acid sequence having about 80% or more sequence identity with the amino acid sequence described in SEQ ID NO: 1.
[2]
The pharmaceutical composition of [1], wherein the psoriasis is plaque psoriasis.
[3]
A pharmaceutical composition for suppressing a skin symptom selected from the group consisting of erythema, thickening, and scaling or desquamation in a patient with psoriasis, comprising substance A.
[A1]
A method of preventing and/or treating psoriasis, comprising administering an effective amount of substance A to a subject.
[A2]
The method of [A1], wherein the psoriasis is plaque psoriasis.
[A3]
A method of suppressing a skin symptom selected from the group consisting of erythema, thickening, and scaling or desquamation in a patient with psoriasis, comprising administering an effective amount of substance A to the patient.
[B1]
Substance A for use in the prevention and/or treatment of psoriasis.
[B2]
The substance A of [B1], wherein the psoriasis is plaque psoriasis.
[B3]
Substance A for use in the suppression of a skin symptom selected from the group consisting of erythema, thickening, and scaling or desquamation in a patient with psoriasis.
[C1]
Use of substance A in the manufacture of a medicament for the prevention and/or treatment of psoriasis.
[C2]
The use of [C1], wherein the psoriasis is plaque psoriasis.
[C3]
Use of substance A in the manufacture of a medicament for the suppression of a skin symptom selected from the group consisting of erythema, thickening, and scaling or desquamation in a patient with psoriasis.

DESCRIPTION OF EMBODIMENTS

Figure 1:
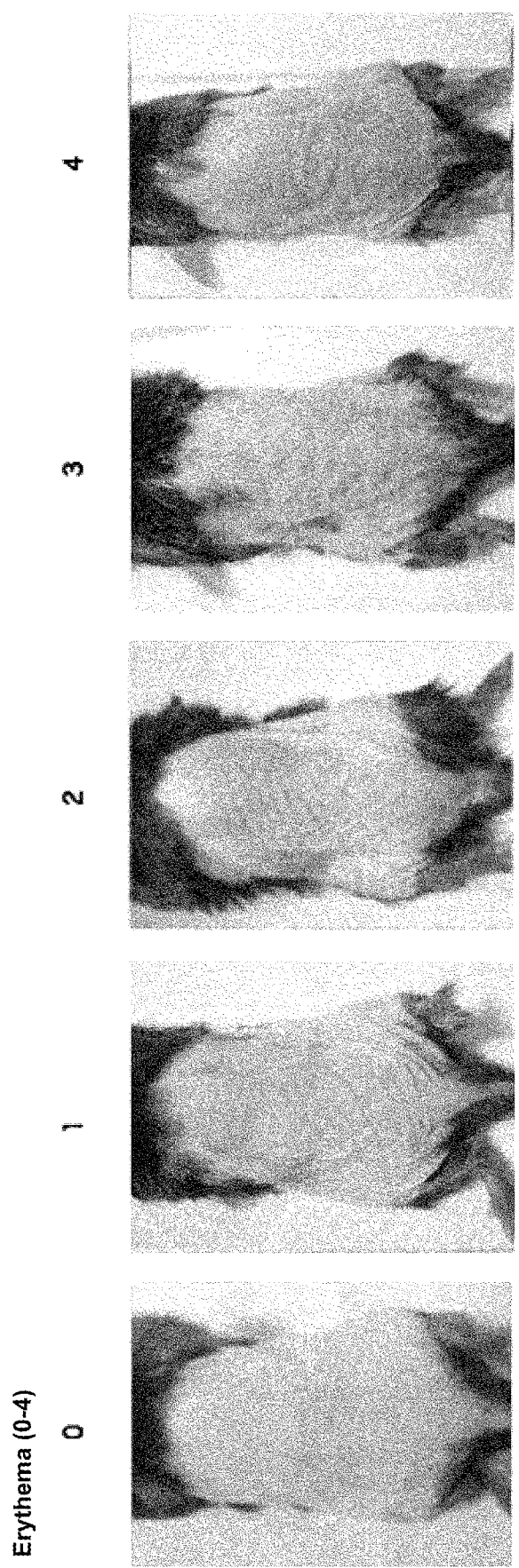
FIG. 1 presents photographs of the back of mice used as a criterion for scoring erythema. The numbers (0-4) above the photographs represent the scores corresponding to the degree of erythema (no symptoms: 0, mild: 1, moderate: 2, severe: 3, and extremely severe: 4).

The present application provides pharmaceutical compositions for the prevention and/or treatment of psoriasis, which comprise an HMGB1 fragment peptide comprising the amino acid sequence described in SEQ ID NO: 1.

In the present application, psoriasis includes, but is not limited to, plaque psoriasis, psoriasis arthropica (psoriatic arthritis), guttate psoriasis, psoriatic erythroderma, and generalized pustular psoriasis. In one embodiment, the psoriasis of the present application is plaque psoriasis.

The main symptoms of plaque psoriasis include "erythema", where the skin becomes red, "thickening (also referred to as infiltration)", where the skin is raised, "scaling", where excessively grown keratin is piled up like scabs, and "desquamation", where the scaling comes off.

In the present application, the term "pharmaceutical composition" is used interchangeably with "medicament", "drug", or "pharmacological composition".

In one embodiment, the pharmaceutical compositions of the present application are used for suppressing a skin symptom selected from the group consisting of erythema, thickening (infiltration), and scaling or desquamation in patients with psoriasis. For example, the pharmaceutical compositions of the present application can be used to suppress these skin symptoms in patients with plaque psoriasis.

In the present application, an HMGB1 fragment peptide comprising the amino acid sequence described in SEQ ID NO: 1 refers to a peptide consisting of a portion of the HMGB1 protein and comprising the amino acid sequence described in SEQ ID NO: 1. Such a peptide can be obtained as genetic recombinants by incorporating DNA encoding the peptide into an appropriate expression system or can be synthesized artificially.

In the present application, examples of the HMGB1 protein include, but are not limited to, proteins comprising the amino acid sequence described in SEQ ID NO: 2 and proteins encoded by DNA comprising the nucleotide sequence described in SEQ ID NO: 3.

Examples of the HMGB1 fragment peptide comprising the amino acid sequence described in SEQ ID NO: 1 in the present application include, but are not limited to, an HMGB1 fragment peptide consisting of the amino acid sequence described in SEQ ID NO: 1.

In the pharmaceutical compositions of the present application, peptides that comprise an amino acid sequence with one or more amino acid residues modified (substituted, deleted, inserted, or added) in the amino acid sequence described in SEQ ID NO: 1 and that are functionally equivalent to an HMGB1 fragment peptide comprising the amino acid sequence described in SEQ ID NO: 1 can be used instead of or in combination with an HMGB1 fragment peptide comprising the amino acid sequence described in SEQ ID NO: 1. Examples of such peptides include, but are not limited to, peptides of the following i) to iv), and peptides of the following i) to iv) and having the effect of preventing and/or treating psoriasis:

i) a peptide comprising an amino acid sequence in which one or more amino acids (e.g., one to ten, one to nine, one to eight, one to seven, one to six, one to five, one to four, one to three, or one or two) have been substituted, deleted, inserted, or added in the amino acid sequence described in SEQ ID NO: 1;

ii) a peptide consisting of an amino acid sequence in which one or more amino acids (e.g., one to ten, one to nine, one to eight, one to seven, one to six, one to five, one to four, one to three, or one or two) have been substituted, deleted, inserted, or added in the amino acid sequence described in SEQ ID NO: 1;

iii) a peptide comprising an amino acid sequence having about 80% or more, for example, about 85% or more, about 90% or more, about 91% or more, about 92% or more, about 93% or more, about 94% or more, about 95% or more, about 96% or more, about 97% or more, about 98% or more, or about 99% or more sequence identity with the amino acid sequence described in SEQ ID NO: 1; and iv) a peptide consisting of an amino acid sequence having about 80% or more, for example, about 85% or more, about 90% or more, about 91% or more, about 92% or more, about 93% or more, about 94% or more, about 95% or more, about 96% or more, about 97% or more, about 98% or more, or about 99% or more sequence identity with the amino acid sequence described in SEQ ID NO: 1.

An effective amount of the peptide of the present application or a pharmaceutical composition comprising the peptide (hereinafter, referred to as the peptide or such) is administered to a subject for the treatment or prevention of the diseases or symptoms described herein.

An effective amount as used herein refers to an amount sufficient for the treatment or prevention of the diseases or symptoms as described herein. Treatment in the present application includes, but is not limited to, alleviation, delay, blockade, improvement, remission, cure, and complete cure. Prevention in the present application includes, but is not limited to, alleviation, delay, and blockade.

Subjects in the present application include, without limitation, mammals, birds, fish, and such. Mammals include, but are not limited to, humans and non-human animals, for example, humans, mice, rats, monkeys, pigs, dogs, rabbits, hamsters, guinea pigs, horses, sheep, and whales. In the present application, the term "subject" is used interchangeably with "patient", "individual", and "animal".

There is no limitation on the site of administration of the peptide or such of the present application, and the peptide or such of the present application can exert its effect when administered to any site, such as a site where a symptom of psoriasis appears or a site nearby, a site different from these sites (a site other than these sites), a site separated from a site where a symptom of psoriasis appears, a site distal from a site where a symptom of psoriasis appears, or a site distal and ectopic to a site where a symptom of psoriasis appears.

The peptide or such of the present application can also exert its effect when administered to any tissue, such as a tissue different from a tissue where a symptom of psoriasis appears (the skin, joint, and such), a tissue separated from a tissue where a symptom of psoriasis appears, a tissue distal from a tissue where a symptom of psoriasis appears, or a tissue distal and ectopic to a tissue where a symptom of psoriasis appears.

Methods of administering the peptide or such of the present application include, but are not limited to, oral administration and parenteral administration. Methods of parenteral administration include, but are not limited to, intravascular (intra-arterial, intravenous, and such), intramuscular, subcutaneous, intradermal, intraperitoneal, nasal, pulmonary, and transdermal administrations. The peptide or such of the present application can also be administered systemically or locally (e.g., subcutaneously, intradermally, or to the skin surface, eyeball or palpebral conjunctiva, nasal mucosa, oral and gastrointestinal mucosa, vaginal and endometrial mucosa, or injured site) by injection administration, for example, intravenous injection, intramuscular injection, intraperitoneal injection, and subcutaneous injection.

Furthermore, in place of the peptide or such of the present application, cells secreting the peptide of the present application, gene therapy vectors into which DNA encoding the peptide has been inserted, and pharmaceutical compositions containing them can be used.

Moreover, the administration method can be appropriately selected according to the age and symptoms of a patient. When administering the peptide of the present application, the dose can be selected, for example, from the range of 0.0000001 mg to 1000 mg per kilogram of body weight per administration. Alternatively, the dose can be selected, for example, from the range of 0.00001 to 100000 mg/body for a patient. When administering cells secreting the peptide of the present application or gene therapy vectors into which DNA encoding the peptide has been inserted, they can be administered so that the amount of the peptide is within the above range. However, the pharmaceutical compositions in the present application are not limited to these dosages.

The pharmaceutical compositions of the present application can be formulated according to conventional methods (e.g., Remington's Pharmaceutical Science, latest edition, Mark Publishing Company, Easton, U.S.A.), and may contain pharmaceutically acceptable carriers and additives together. Examples include, but are not limited to, surfactants, excipients, coloring agents, perfumes, preservatives, stabilizers, buffers, suspending agents, isotonizing agents, binding agents, disintegrants, lubricants, fluidity-promoting agents, and flavoring agents. Other commonly used carriers can also be used as appropriate. Specific examples include, light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain fatty acid triglycerides, polyoxyethylene hydrogenated castor oil 60, white sugar, carboxymethyl cellulose, cornstarch, and inorganic salts.

All prior art documents cited herein are incorporated herein as references.

The present invention is further illustrated by, but not limited to, the examples below.

EXAMPLE

Example 1

Efficacy Evaluation of an HMGB1 Fragment Peptide for Psoriasis (1)
(1) Materials and Methods
i) Drug Preparation In order to induce psoriasis using imiquimod, a cream containing 5% imiquimod (Beselna Cream 5%, manufactured by Mochida Pharmaceutical Co., Ltd.) was used. Imiquimod is represented as IMQ in the drawings corresponding to the Examples of this application. A peptide consisting of amino acid residues 1-44 of the human-derived HMGB1 protein (SEQ ID NO: 1) was chemically synthesized by a solid-phase method. Hereinafter, the HMGB1 fragment peptide is referred to as the HMGB1 peptide (1-44) and is expressed as an abbreviation "1-44" in the drawings corresponding to the Examples.

ii) Production of Psoriasis Model Mice

C57BL/6 mice (7-week-old, female, body weight about 20 g) were prepared, and the hair on the back was removed. In order to induce psoriasis, the cream containing 5% imiquimod was applied to the dorsal skin of the mice at a dose of 1.25 g/animal/day (62.5 mg/animal/day as imiquimod) once a day for four days. In the following, the day when imiquimod was first applied is represented as "the 1st day of the start of imiquimod application (Day 1)", and the next day onward is represented as "the Xth day from the start of imiquimod application (Day X)". That is, the last day that imiquimod was applied was the 4th day from the start of imiquimod application (Day 4), and no application was performed on the 5th day from the start of imiquimod application (Day 5).

iii) Peptide Administration

The psoriasis model mice produced as described above were divided into the HMGB1 peptide (1-44) administration group (n=3) and the control group (n=3). The test substance was administered by injecting an HMGB1 peptide (1-44) solution, which has been adjusted to a concentration of 1 μg/μl with saline as the vehicle, into the vein at a dose of 100 μl/day (5 mg/kg/day as the peptide dose) for three days from the 1st day of the start of imiquimod application (Day 1). In the control group, saline was injected into the vein at a dose of 100 μl/day for three days from the 1st day of the start of imiquimod application.

iv) Evaluation of the Effect of Peptide Administration

The degree of the symptoms of psoriasis on the dorsal skin of the mice was evaluated by the PASI score for five days from the 1st day of the start of imiquimod application. The PASI score was calculated by quantifying the degree of each of (a) erythema, (b) scaling (desquamation), and (c) thickening (infiltration) of skin using five stages, [no symptoms: 0 points, mild: 1 point, moderate: 2 points, severe: 3 points, and extremely severe: 4 points], and summing up the values of (a), (b), and (c) (minimum 0 points-maximum 12 points).

Figure 2:
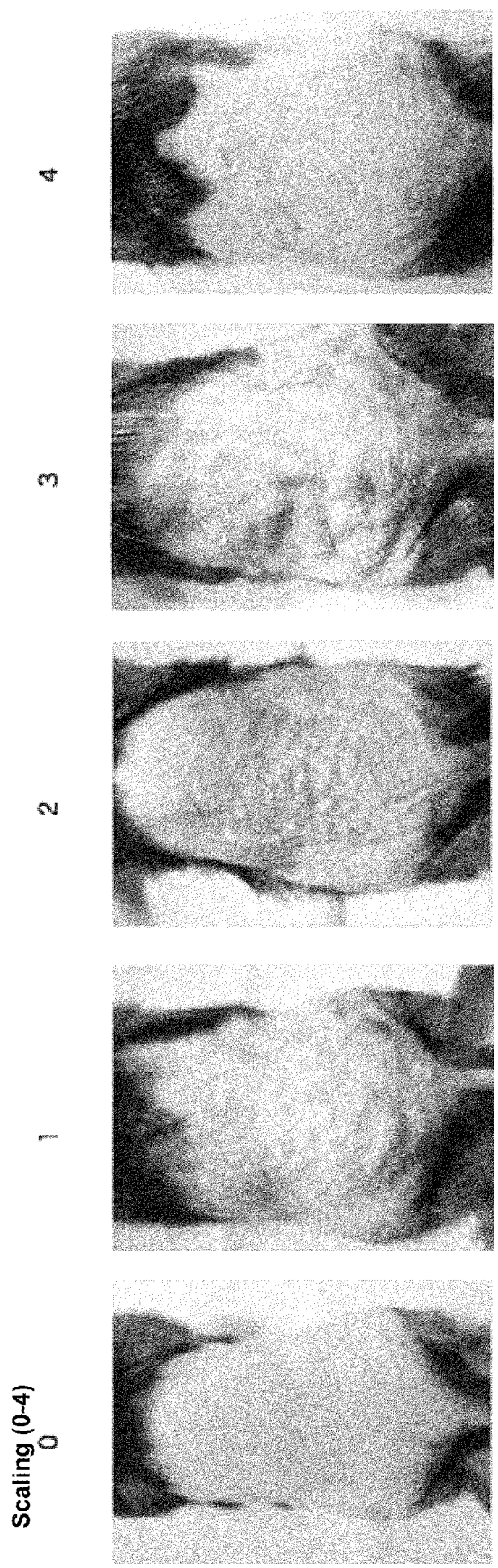
FIG. 2 presents photographs of the back of mice used as a criterion for scoring scaling. The numbers (0-4) above the photographs represent the scores corresponding to the degree of scaling (no symptoms: 0, mild: 1, moderate: 2, severe: 3, and extremely severe: 4).

(a) The erythema score was determined by using the photographs of the back of mice shown in FIG. 1 as a criterion for each score and visually comparing them with the condition of the back of the mice to be evaluated. (b) The scaling score was determined by using the photographs of the back of mice shown in FIG. 2 as a criterion for each score and visually comparing them with the condition of the back of the mice to be evaluated. (c) The thickening score was determined as follows: Two measurement sites were determined on the back of the mice, the skin was pinched and its thickness was measured with a caliper, and the average value from the two sites was recorded daily as the skin thickness (mm). Quantification was carried out by giving 0 points when the value of skin thickness of each day relative to the skin thickness on the 1st day of the start of imiquimod application (before application) was less than 1.1, 1 point when the value was 1.1 or more to less than 1.3, 2 points when the value was 1.3 or more to less than 1.5, 3 points when the value was 1.5 or more to less than 1.7, and 4 points when the value was 1.7 or more.

On the 5th day from the start of imiquimod application (Day 5), the dorsal skin of the mice was collected, mRNA was extracted from the skin, and the expression levels of the inflammatory cytokines (IL-6, IL-17F, and IL-22), which are known to be involved in the pathogenesis of psoriasis, were analyzed by quantitative PCR.

(2) Results i) PASI Score

Figure 3:
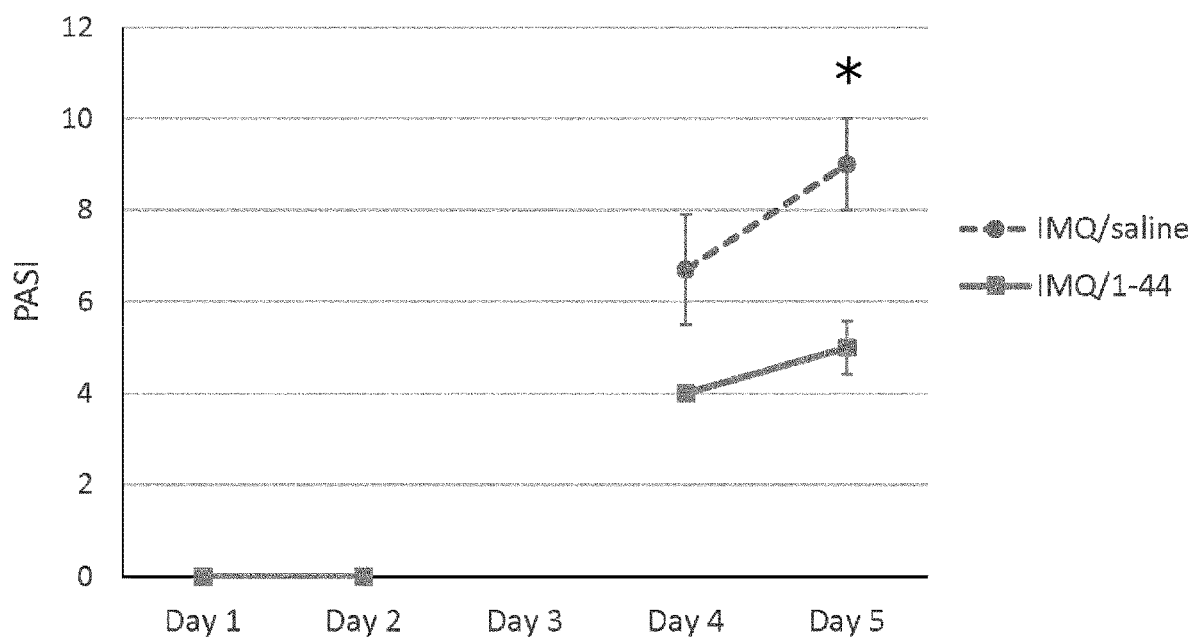
FIG. 3 is a graph showing the change in the PAST score after the start of imiquimod application. The PAST score on the 5th day from the start of imiquimod application (Day 5) was significantly different between the control group (see "IMQ/saline") and the HMGB1 peptide (1-44) administration group (see "IMQ/1-44") (*p<0.05). On Day 3, the PAST score is shown as a missing value because the value of measuring skin thickness could not be obtained due to a problem with the measuring instrument.
Figure 4:
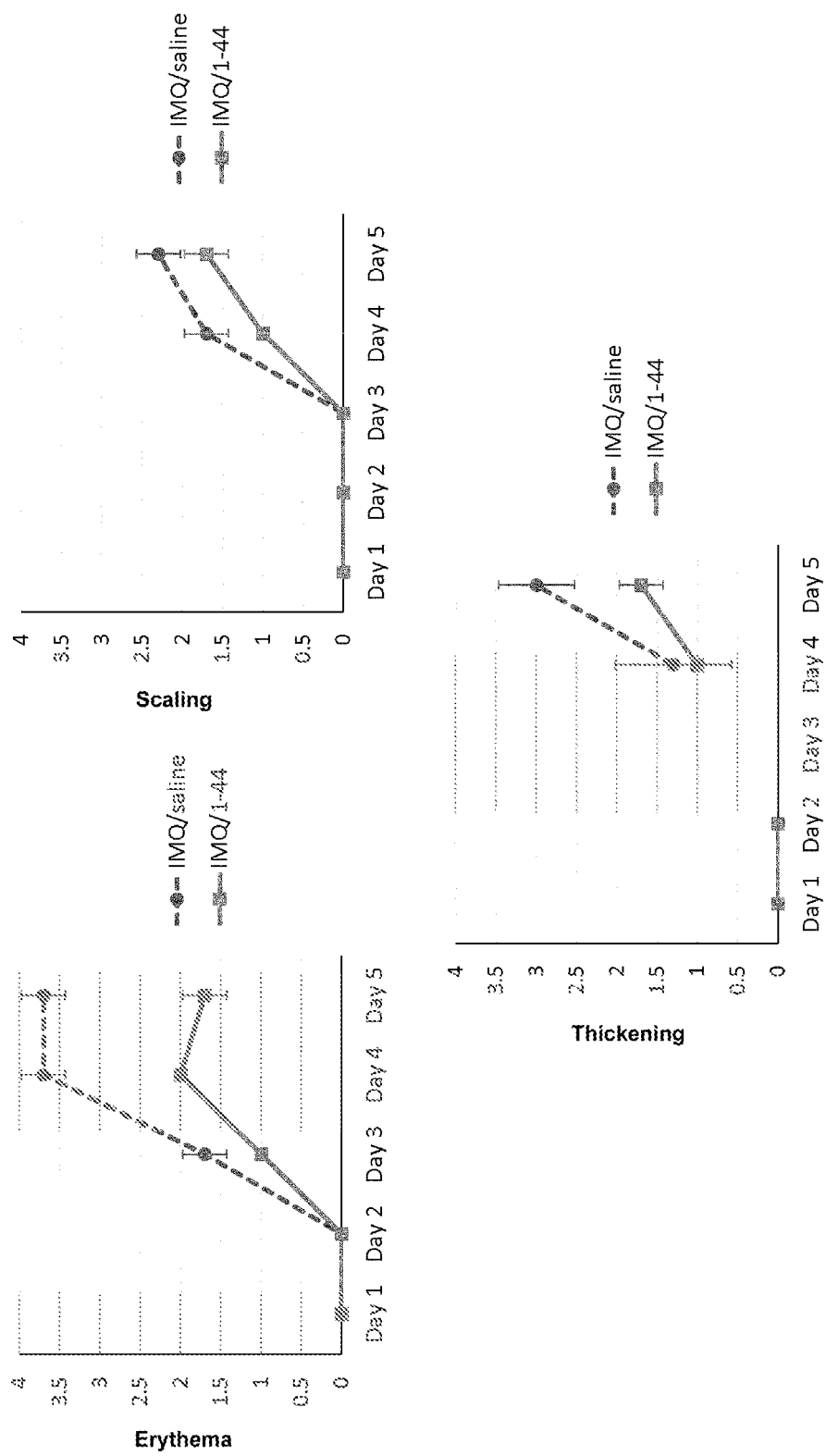
FIG. 4 presents graphs showing the changes in the erythema, scaling, and thickening scores after the start of imiquimod application. On Day 3, the thickening score is shown as a missing value because the value of measuring skin thickness could not be obtained due to a problem with the measuring instrument.
Figure 5:
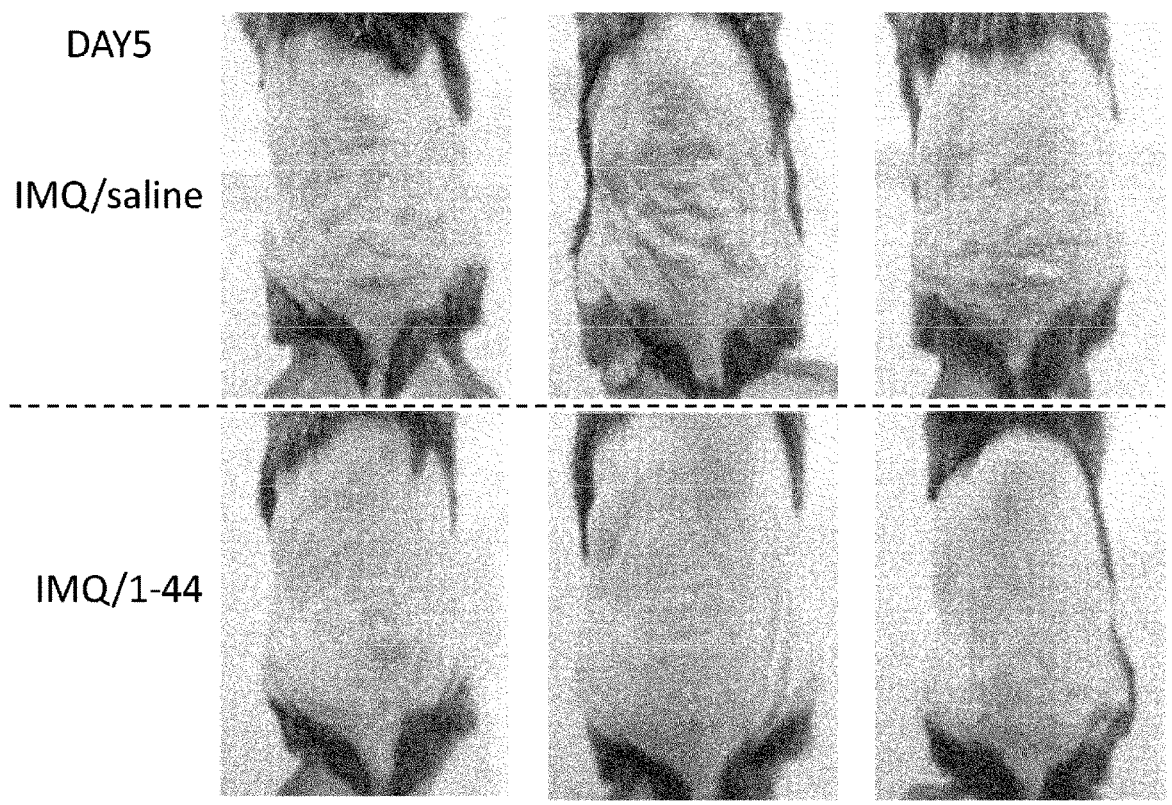
FIG. 5 presents photographs of the back of the mice on the 5th day from the start of imiquimod application.

FIG. 3 and FIG. 4 respectively show the changes in the PASI score and the scores for each item of erythema, scaling, and thickening up to the 5th day from the start of imiquimod application (see "IMQ/saline" for the control group and "IMQ/1-44" for the HMGB1 peptide (1-44) administration group). From the 3rd day or the 4th day from the start of imiquimod application, the PASI score as well as the erythema, scaling, and thickening scores tended to increase as the days passed in both the control group and the HMGB1 peptide (1-44) administration group. However, all these scores in the HMGB1 peptide (1-44) administration group were lower than those in the control group. In particular, the PASI score in the HMGB1 peptide (1-44) administration group was significantly lower than that in the control group on the 5th day from the start of imiquimod application. The photographs of the back of the mice on the 5th day from the start of imiquimod application are shown in FIG. 5 (see "IMQ/saline" for the control group and "IMQ/1-44" for the HMGB1 peptide (1-44) administration group). These results indicate that the administration of the HMGB1 peptide (1-44) suppressed the skin symptoms in the psoriasis model mice.

ii) Expression Levels of Inflammatory Cytokines

Figure 6:
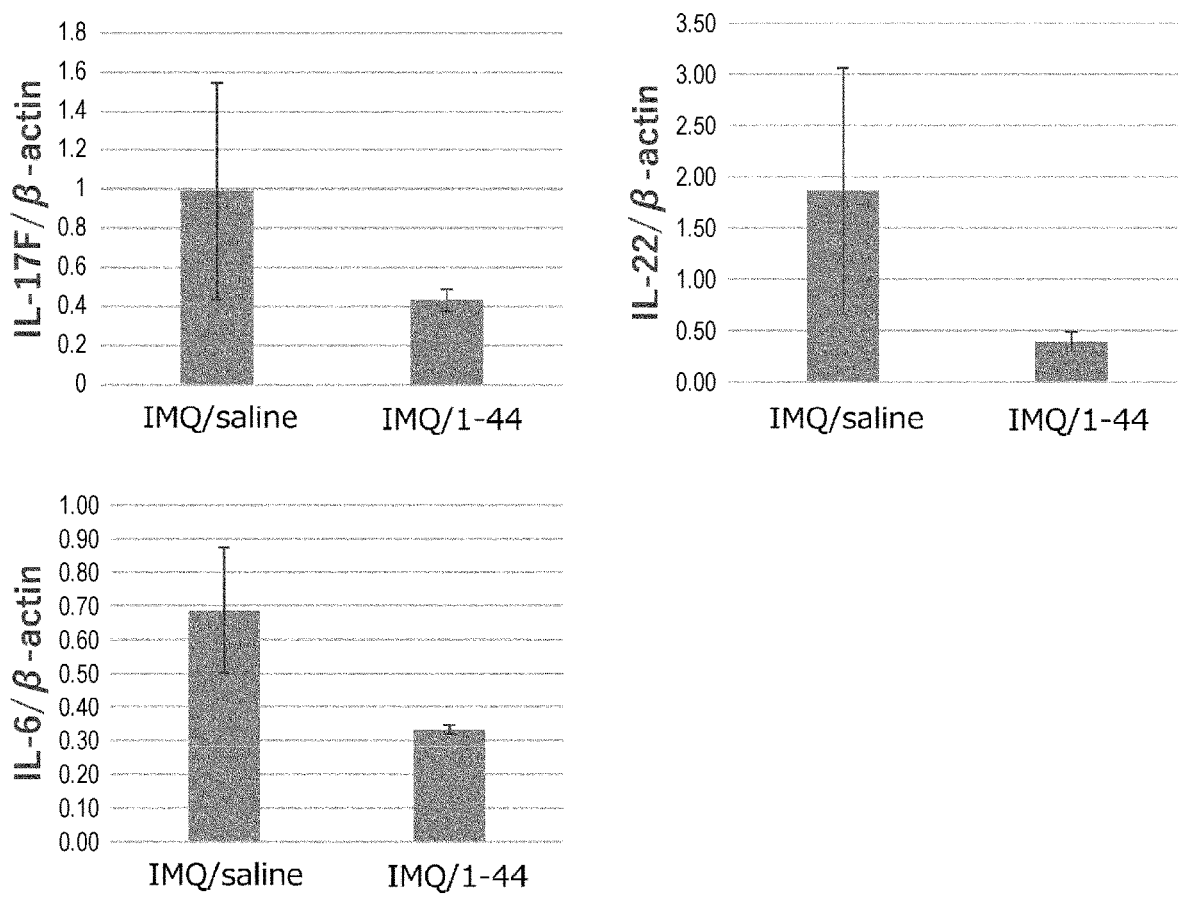
FIG. 6 presents graphs showing the expression levels of the inflammatory cytokines in the skin on the 5th day from the start of imiquimod application.

FIG. 6 shows the expression levels of the inflammatory cytokines in the skin on the 5th day from the start of imiquimod application (see "IMQ/saline" for the control group and "IMQ/1-44" for the HMGB1 peptide (1-44) administration group). The expression levels of all of IL-6, IL-17F, and IL-22 in the HMGB1 peptide (1-44) administration group were lower than those in the control group.

Example 2

Efficacy Evaluation of an HMGB1 Fragment Peptide for Psoriasis (2)

(1) Materials and Methods i) Drugs, Mice, and Peptide Administration

The drugs were prepared and the psoriasis model mice were produced in the same way as Example 1. The peptides were administered in the same way as Example 1 except that the number of mice was changed to six in both the HMGB1 peptide (1-44) administration group and the control group.

ii) Evaluation of the Effect of Peptide Administration

The degree of the symptoms of psoriasis on the dorsal skin of the mice was evaluated by the PASI score for four days from the 1st day of the start of imiquimod application. The PASI score was calculated in the same manner as Example 1.

On the 5th day from the start of imiquimod application, the dorsal skin of the mice was collected, mRNA was extracted from the skin, and the expression levels of the inflammatory cytokines (IL-1$\beta$, IL-6, IL-17A, IL-17F, and IL-22), which are known to be involved in the pathogenesis of psoriasis, were analyzed by quantitative PCR.

(2) Results i) PAST Score

Figure 7:
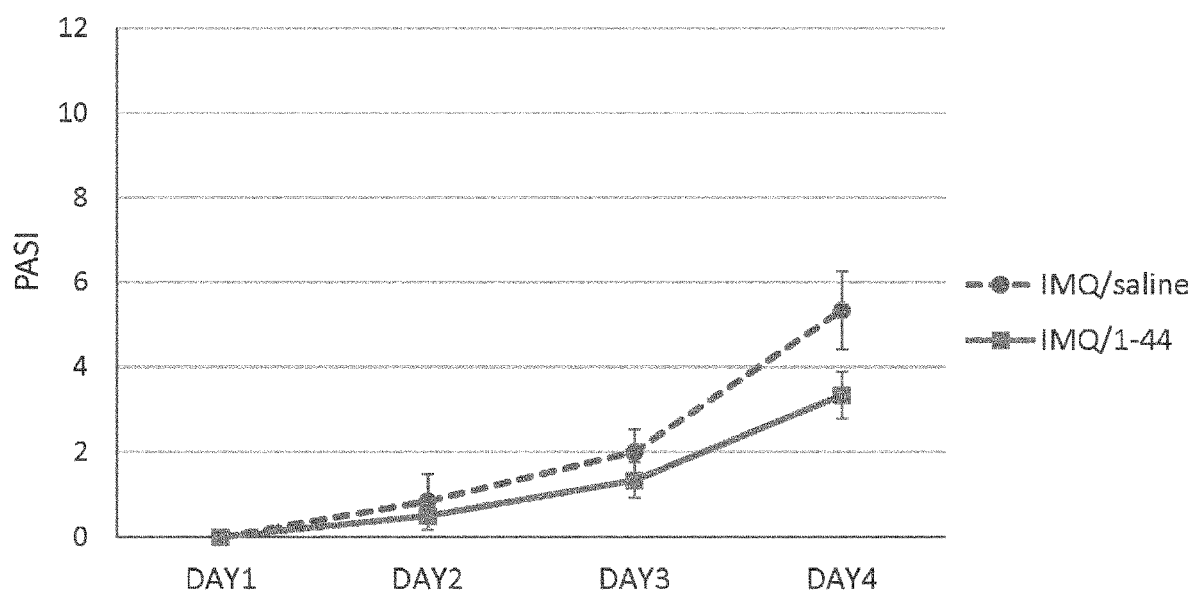
FIG. 7 is a graph showing the change in the PAST score after the start of imiquimod application.

FIG. 7 shows the change in the PASI score up to the 4th day from the start of imiquimod application (see "IMQ/saline" for the control group and "IMQ/1-44" for the HMGB1 peptide (1-44) administration group). From the 2nd day from the start of imiquimod application, the PASI score increased as the days passed in both the control group and the HMGB1 peptide (1-44) administration group. However, the PAST score in the HMGB1 peptide (1-44) administration group was lower than that in the control group (FIG. 7). The result indicates that the administration of the HMGB1 peptide (1-44) suppressed the skin symptoms in the psoriasis model mice.

ii) Expression Levels of Inflammatory Cytokines

Figure 8:
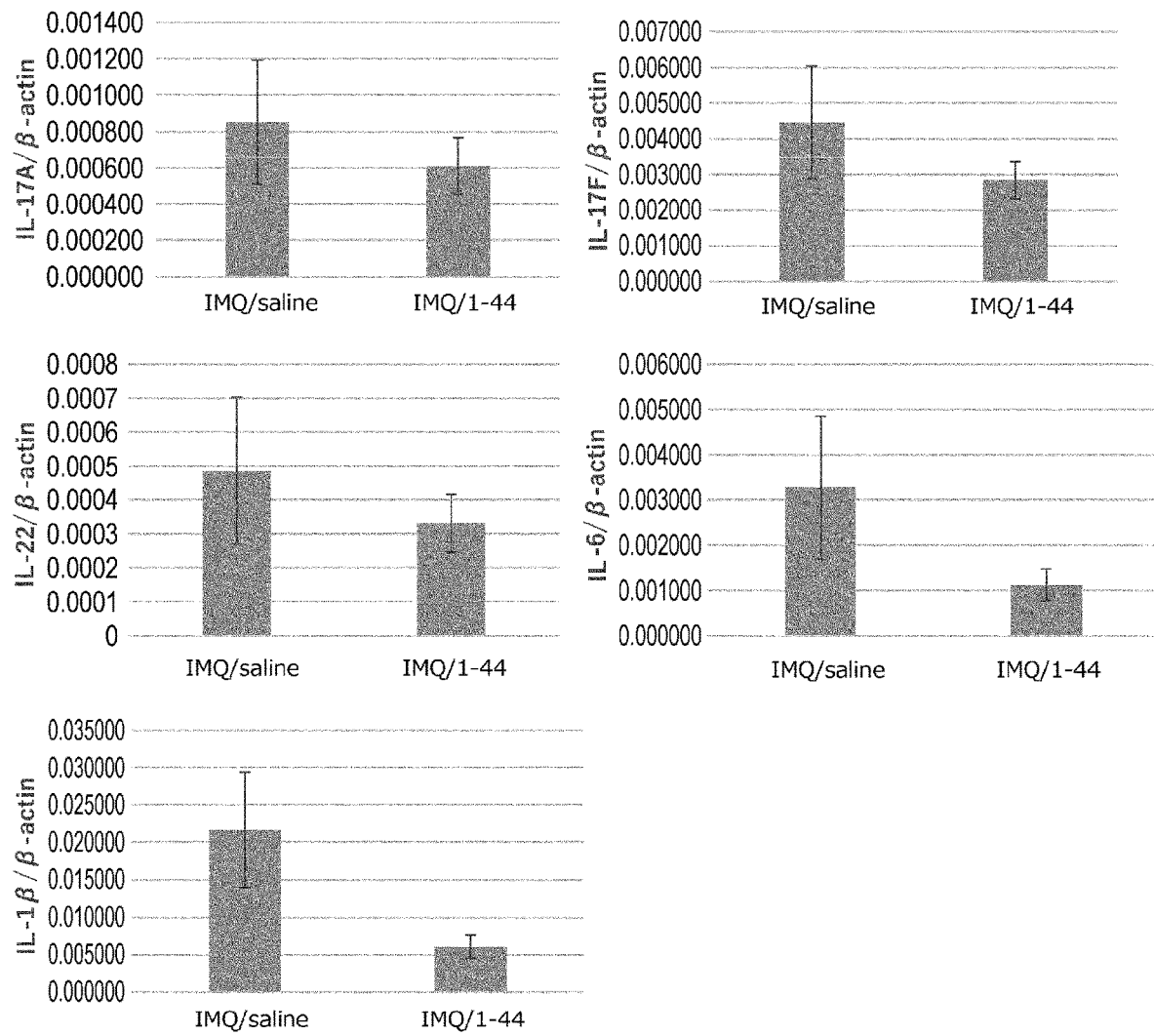
FIG. 8 presents graphs showing the expression levels of the inflammatory cytokines in the skin on the 5th day from the start of imiquimod application.

FIG. 8 shows the expression levels of the inflammatory cytokines in the skin on the 5th day from the start of imiquimod application (see "IMQ/saline" for the control group and "IMQ/1-44" for the HMGB1 peptide (1-44) administration group). The expression levels of all of IL-1$\beta$, IL-6, IL-17A, IL-17F, and IL-22 in the HMGB1 peptide (1-44) administration group were lower than those in the control group.

INDUSTRIAL APPLICABILITY

Pharmaceutical compositions comprising the peptide of the present application are expected to provide great benefits to patients with psoriasis who cannot obtain a sufficient effect with existing therapeutics.

The invention claimed is:

1. A method of treating psoriasis, comprising administering to a patient with psoriasis an effective amount of a peptide selected from the group consisting of:
   (a) a peptide consisting of the amino acid sequence of SEQ ID NO: 1; and
   (b) a peptide consisting of the amino acid sequence of SEQ ID NO: 1 with one or two additional amino acids and having an effect of suppressing erythema, thickening, and scaling of the skin in a subject with psoriasis.

2. The method of claim 1, wherein the psoriasis is plaque psoriasis.

3. The method of claim 1, wherein the peptide is selected from the group consisting of:
   (a) a peptide consisting of the amino acid sequence of SEQ ID NO: 1; and
   (b) a peptide consisting of the amino acid sequence of SEQ ID NO: 1 with one additional amino acid and having an effect of suppressing erythema, thickening, and scaling of the skin in a subject with psoriasis.

4. The method of claim 1, wherein the peptide is a peptide consisting of the amino acid sequence of SEQ ID NO: 1.

5. A method of suppressing a skin symptom selected from the group consisting of erythema, thickening, scaling and desquamation in a patient with psoriasis, comprising administering to the patient an effective amount of a peptide selected from the group consisting of:
   (a) a peptide consisting of the amino acid sequence of SEQ ID NO: 1; and
   (b) a peptide consisting of the amino acid sequence of SEQ ID NO: 1 with one or two additional amino acids and having an effect of suppressing erythema, thickening, and scaling of the skin in a subject with psoriasis.

6. The method of claim 5, wherein the peptide is selected from the group consisting of:
   (a) a peptide consisting of the amino acid sequence of SEQ ID NO: 1; and
   (b) a peptide consisting of the amino acid sequence of SEQ ID NO: 1 with one additional amino acid and having an effect of suppressing erythema, thickening, and scaling of the skin in a subject with psoriasis.

7. The method of claim 5, wherein the peptide is a peptide consisting of the amino acid sequence of SEQ ID NO: 1.

* * * * *

SEQUENCE LISTING

```
Sequence total quantity: 3
SEQ ID NO: 1            moltype = AA  length = 44
FEATURE                 Location/Qualifiers
REGION                  1..44
                        note = An artificially synthesized peptide sequence
source                  1..44
                        mol_type = protein
                        organism = synthetic construct
SEQUENCE: 1
MGKGDPKKPR GKMSSYAFFV QTCREEHKKK HPDASVNFSE FSKK             44

SEQ ID NO: 2            moltype = AA  length = 215
FEATURE                 Location/Qualifiers
source                  1..215
                        mol_type = protein
                        organism = Homo sapiens
SEQUENCE: 2
MGKGDPKKPR GKMSSYAFFV QTCREEHKKK HPDASVNFSE FSKKCSERWK TMSAKEKGKF    60
EDMAKADKAR YEREMKTYIP PKGETKKKFK DPNAPKRPPS AFFLFCSEYR PKIKGEHPGL   120
SIGDVAKKLG EMWNNTAADD KQPYEKKAAK LKEKYEKDIA AYRAKGKPDA AKKGVVKAEK   180
SKKKKEEEED EEDEEDEEEE EDEEDEDEEE DDDDE                             215

SEQ ID NO: 3            moltype = DNA  length = 648
FEATURE                 Location/Qualifiers
source                  1..648
                        mol_type = unassigned DNA
                        organism = Homo sapiens
SEQUENCE: 3
atgggcaaag gagatcctaa gaagccgaga ggcaaaatgt catcatatgc attttttgtg    60
caaacttgtc gggaggagca taagaagaag cacccagatg cttcagtcaa cttctcagag   120
ttttctaaga agtgctcaga gaggtggaag accatgtctg ctaaagagaa aggaaaattt   180
gaagatatgg caaagcgga caaggcccgt tatgaaagag aaatgaaaac ctatatccct   240
cccaaagggg agacaaaaaa gaagttcaag gatcccaatg cacccaagag gcctccttcg   300
gccttcttcc tcttctgctc tgagtatcgc ccaaaaatca aggagaaca tcctggcctg   360
tccattggtg atgttgcgaa gaaactggga gagatgtgga ataacactgc tgcagatgac   420
aagcagcctt atgaaaagaa ggctgcgaag ctgaaggaaa atacgaaga ggatattgct   480
gcatatcgag ctaaaggaaa gcctgatgca gcaaaaaagg gagttgtcaa ggctgaaaaa   540
agcaagaaaa agaaggaaga ggaggaagat gaggaagatg aagaggatga ggaggaggag   600
gaagatgaag aagatgaaga tgaagaagaa gatgatgatg atgaataa              648
```